(12) United States Patent
Tor et al.

(10) Patent No.: US 11,702,442 B2
(45) Date of Patent: Jul. 18, 2023

(54) CYCLIC DINUCLEOTIDE COMPOUNDS AS STING AGONISTS

(71) Applicant: The Regents of the University of California, Oakland, CA (US)

(72) Inventors: Yitzhak Tor, San Diego, CA (US); Yao Li, San Diego, CA (US); Andrea Fin, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 329 days.

(21) Appl. No.: 17/005,045

(22) Filed: Aug. 27, 2020

(65) Prior Publication Data

US 2021/0101924 A1 Apr. 8, 2021

Related U.S. Application Data

(60) Provisional application No. 62/892,341, filed on Aug. 27, 2019.

(51) Int. Cl.
| | |
|---|---|
| *A01N 43/04* | (2006.01) |
| *A61K 31/70* | (2006.01) |
| *C07H 21/02* | (2006.01) |
| *A61K 39/00* | (2006.01) |
| *A61P 37/04* | (2006.01) |
| *C07H 21/04* | (2006.01) |

(52) U.S. Cl.
CPC ............ *C07H 21/02* (2013.01); *A61K 39/00* (2013.01); *A61P 37/04* (2018.01); *C07H 21/04* (2013.01)

(58) Field of Classification Search
None
See application file for complete search history.

(56) References Cited

U.S. PATENT DOCUMENTS

2020/0369711 A1\* 11/2020 Beigelman ............. C07H 21/02

OTHER PUBLICATIONS

Kalia, D. et al. (Jan. 7, 2013, e-published Sep. 28, 2012). "Nucleotide, c-di-GMP, c-di-AMP, cGMP, cAMP, (p)ppGpp signaling in bacteria and implications in pathogenesis," *Chem Soc Rev* 42(1):305-341.
Li, Y. et al. (May 12, 2020, e-published Apr. 28, 2020). "Enzymatic Syntheses and Applications of Fluorescent Cyclic Dinucleotides," *Chemistry* 26(27):6076-6084.
Li, Y. et al. (Sep. 14, 2020). "Tuning the Innate Immune Response to Cyclic Dinucleotides by Using Atomic Mutagenesis," *Chembiochem* 21(18):2595-2598.
Ludford, P.T 3$^{rd}$, et al. (Mar. 1, 2019, e-published Feb. 21, 2019). "Fluorescing Isofunctional Ribonucleosides: Assessing Adenosine Deaminase Activity and Inhibition," *ChemBioChem* 20(5):718-726.
LV, Y. et al. (Sep. 13, 2019). "Highly Efficient Preparation of Cyclic Dinucleotides via Engineering of Dinucleotide Cyclases in *Escherichia coli*," *Front Microbiol* 10:2111.
Novotná, B. et al. (Dec. 12, 2019, e-published Nov. 27, 2019). "Enzymatic Preparation of 2'-5',3'-5'-Cyclic Dinucleotides, Their Binding Properties to Stimulator of Interferon Genes Adaptor Protein, and Structure/Activity Correlations," *J Med Chem* 62(23):10676-10690.
Whiteley, A.T. et al. (Mar. 2019, e-published Feb. 20, 2019). "Bacterial cGAS-like enzymes synthesize diverse nucleotide signals," *Nature* 567(7747):194-199.

\* cited by examiner

*Primary Examiner* — Patrick T Lewis
(74) *Attorney, Agent, or Firm* — Mintz, Levin, Cohn, Ferris, Glovsky and Popeo, P.C.

(57) ABSTRACT

The disclosure provides cyclic dinucleotides that are useful as STING agonists, pharmaceutical compositions and vaccines comprising the cyclic dinucleotides, and methods of treating diseases and disorders using the cyclic dinucleotides, pharmaceutical compositions, and vaccines.

18 Claims, 10 Drawing Sheets

CYCLIC DINUCLEOTIDE COMPOUNDS AS STING AGONISTS

CROSS-REFERENCES TO RELATED APPLICATIONS

This application claims priority under 35 USC § 120 to U.S. Application No. 62/892,341 filed Aug. 27, 2019, the disclosure of which is incorporated by reference herein

STATEMENT AS TO RIGHTS TO INVENTIONS MADE UNDER FEDERALLY SPONSORED RESEARCH AND DEVELOPMENT

This invention was made with government support under grant numbers GM069773 and GM 124589 awarded by the National Institutes of Health. The government has certain rights in the invention.

BACKGROUND

Stimulator of interferon genes (STING) is known to be a central mediator of innate immunity. The STING protein expressed in various endothelial and epithelial cell types as well as in hematopoietic cells such as T cells, macrophages and dendritic cells. STING is naturally activated by aberrant DNA species via formation of native cyclic dinucleotides (CDNs) in cytosol of the cell. When stimulated STING induces the expression of type I interferon (IFN), cytokines and T cell recruitment factors that result in the activation of macrophages and dendritic cells, innate effector cells such as natural killer (NK) cells and priming of tumor specific T cells. Recent studies have shown that the STING pathway is essential for radiation induced and spontaneous natural antitumor T cell responses. Tumor cells often induce an immunosuppressive microenvironment favoring cancer development. Targeting the STING pathway by using STING agonists to produce IFNs for enhancing antitumor immune response may provide an alternative strategy for the improvement of cancer immunotherapy. The disclosure is directed to these, as well as other, important ends.

BRIEF SUMMARY

The disclosure provides STING agonists, pharmaceutical compositions and vaccines comprising STING agonists, and methods of using the STING agonists to treat various diseases and disorders. The disclosure provides STING agonists that are compounds of Formula (I), compounds of Formula (II), compounds of Formula (III), stereoisomers of compounds of Formula (I), (II), or (III), pharmaceutically acceptable salts of compounds of Formula (I), (II), or (III), and pharmaceutically acceptable salts of stereoisomers of compounds of Formula (I), (II), or (III). The disclosure provides pharmaceutical compositions comprising the STING agonists described herein and a pharmaceutically acceptable excipient. The disclosure provides vaccines comprising the STING agonists described herein and an adjuvant. The disclosure provides methods of activating an immune response and activating a STING protein by administering to a patient any of the STING agonists, pharmaceutical compositions, or vaccines described herein. The disclosure provides methods of treating cancer, an autoimmune disease, an infectious disease, or a viral disease in a patient in need thereof by administering to a patient any of the STING agonists, pharmaceutical compositions, or vaccines described herein.

These and other embodiments and aspects of the disclosure are described in detail herein.

BRIEF DESCRIPTION OF THE DRAWINGS

FIG. 2A shows IRF3 phosphorylation induced by c-di-GMP analogues. 1, 5 and 10 μM of each CDN was used to transfect RAW 264.7 cells. Cells were lysed with NP-40 lysis buffer 2 h post transfection, 20 μg of total protein was loaded on SDS-polyacrylamide gel. Proteins were transferred to PVDF membrane after gel electrophoresis, and immunoblotted against pIRF3 and β-actin. FIG. 2B shows quantification of western blot. The y-axis indicates relative intensity of pIRF3 compare to β-actin.

FIG. 3A shows IFN production induced by c-di-GMP and its analogues. RAW 264.7 cells were transfected with 1, 5, 10 μM of c-di-GMP, c-di-$^{tz}$GMP, c-G$^{th}$GMP, c-di-G$^{th}$GMP and c-G$^{tz}$GMP, and incubated for 2, 4, 6 h before being lysed by TRIzol. RNA purification and RT-qPCR were conducted following the protocol described in the Experimental Section. FIG. 3B show IFN response after 2, 4, 6 h of incubation with 5 μM of CDNs. FIG. 3C shows IFN response to 1, 5, and 10 μM of CDNs after 2 h of incubation. Two independent assays were performed in triplicates (n=2). Error bars indicate SD. See Yi et al, Tuning the Innante Immune Response to Cyclic Dinucleotides by Using Atomic Mutagenesis, ChemBioChem, Volume 21 (2020).

FIG. 6A: UV-monitored HPLC chromatograms (260 nm) of the DncV-mediated synthesis of c-di-GMP. FIG. 6B: HR-MS of the intermediates from CIAP-treated reaction. FIG. 6C: Kinetic analysis of the HPLC-integrated relative concentration and fitted curve of the starting materials (measured as nucleosides), products and intermediates for the DncV-mediated reactions of GTP. FIGS. 6D-6F: HPLC chromatograms (333 nm), HR-MS of the intermediate, and kinetic analysis of DncV-mediated synthesis of c-di-$^{tz}$GMP. FIGS. 6G-6I: HPLC chromatograms (321 nm), HRMS of the intermediate, and kinetic analysis of DncV-mediated synthesis of c-di-$^{th}$GMP. Aliquots were treated with calf intestinal alkaline phosphatase (CIAP) at designated times, therefore the starting materials were presented as G, $^{tz}$G and $^{th}$G, and intermediates were presented as GpG, $^{tz}$Gp$^{tz}$G and $^{th}$Gp$^{th}$G. Assays were done in duplicates. Error bars indicate standard deviation (SD).

FIG. 11A: rocR-mediated c-G$^{th}$GMP hydrolysis monitored with steady-state emission spectra. FIG. 11B: rocR-mediated c-G$^{tz}$GMP hydrolysis monitored with steady-state emission spectra. The y-scale was integrated emission intensity (area under the curve). Assays were done in triplicates or duplicates (error bars, indicating SD, were smaller than the points shown).

(FIG. 13B) c-GtzGMP; and (FIG. 13C) c-di-tzGMP. Excitation wavelength was 380 nm for all emission spectra. Spectra were measured under the conditions described herein for CDN hydrolysis monitored with steady-state fluorescence spectroscopy.

Figure 1:
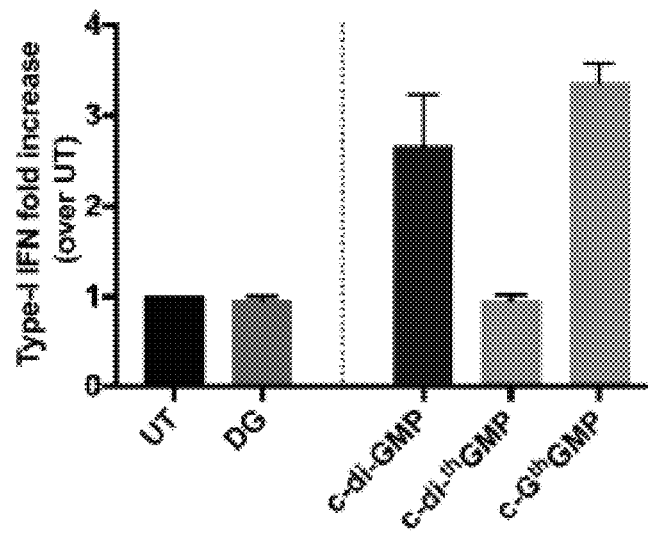
FIG. 1 shows type-I IFN induced by CDNs in THP-1 cells. THP-1 cells were seeded at a density of 100000 cells/well in a 96-well cell culture plate and differentiated with 25 nM of PMA for approximately 20 h prior to treatment with CDNs. Cells were transfected with 5 μM of CDNs in a permeabilization buffer containing 5 μg/mL of digitonin, then washed and incubated in RPMI medium with 2% FBS at 37° C. for 4 h. 50 μL of cell culture supernatant per well was transferred to 150 μL of HEK-Blue IFN α/β reporter cells seeded at 50000 cells/well in a 96-well cell culture plate and incubated at 37° C. overnight. The reporter cells were spun down the next day, and 50 μL of cell culture supernatant per well was transferred to a 96-well plate and added with 150 μL of QUANTI-Blue™ SEAP detection medium (InvivoGen). The samples were then incubated at 37° C. for 1 h 20 min before absorption was measured at 640 nm. The absorption signal of each sample was normalized to untreated samples. Two independent assays were performed in duplicate or triplicate. Error bars indicate SD.

Color versions of FIG. 3 can be found in Li et al, Tuning the Innate Immune Response of Cyclic Dinucleotides by Using Atomic Mutgenesis, ChemBioChem, Volume 21 (Apr. 28, 2020). Color versions of FIGS. 4 and 6-12 can be found in Li et al, "Enzymatic Syntheses and Applications of Fluorescent Cyclic Dinucleotides," Chem Eur. J. 26:6076-6084 (Apr. 28, 2020), the disclosure of which is incorporated by reference herein in its entirety.

DETAILED DESCRIPTION

Definitions

"STING" or "stimulator of interferon genes protein" refers to any synthetic or naturally occurring forms, variants or homologs of STING that maintain the protein activity (e.g., within at least 50%, 80%, 90%, 95%, 96%, 97%, 98%, 99% or 100% activity compared to the native protein). In embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, STING is the human protein as identified by its UniProtKB reference number Q86WV6. In embodiments, STING is the human protein as identified by its UniProtKB reference number Q86WV6, or a homolog or functional fragment thereof. In embodiments, STING is STING isoform 1 identified by its GenBank accession number AZQ04904.1. In embodiments, STING is STING isoform 2 identified by its GenBank accession number AZQ04905.1. In embodiments, STING is STING isoform 3 identified by its GenBank accession number AZQ04906.1. In embodiments, STING is STING isoform X2 identified by its NCBI reference sequence XP_011535941.1.

"DncV" or "*Vibrio cholerae* dinucleotide cyclase" or "cyclic GMP-AMP synthase" refer to any synthetic to naturally occurring forms, variants or homologs of DncV that maintain the protein activity (e.g., within at least 50%, 80%, 90%, 95%, 96%, 97%, 98%, 99% or 100% activity compared to the native protein). In embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, DncV is the protein as identified by its UniProtKB reference number Q9KVG7. In embodiments, DncV is the protein as identified by its UniProtKB reference number Q9KVG7, or a homolog or fragment thereof. In embodiments, DncV is the protein as identified by its NCBI sequence reference WP_119783399.1. In embodiments, DncV is the protein as identified by its NCBI sequence reference WP_119783399.1, or homolog or functional fragment thereof. In embodiments, DncV is the protein as identified by its NCBI sequence reference WP_119474606.1. In embodiments, DncV is the protein as identified by its NCBI sequence reference WP_119474606.1, or homolog or functional fragment thereof. In embodiments, DncV is the protein as identified by its NCBI sequence reference WP_119471652.1. In embodiments, DncV is the protein as identified by its NCBI sequence reference WP_119471652.1, or homolog or functional fragment thereof. In embodiments, DncV is the protein as identified by its NCBI sequence reference WP_119467176.1. In embodiments, DncV is the protein as identified by its NCBI sequence reference WP_119467176.1, or homolog or functional fragment thereof. In embodiments, DncV is the protein as identified by its NCBI sequence reference WP_088124767.1. In embodiments, DncV is the protein as identified by its NCBI sequence reference WP_088124767.1, or homolog or functional fragment thereof. In embodiments, DncV is the protein as identified by its NCBI sequence reference WP_053025835.1. In embodiments, DncV is the protein as identified by its NCBI sequence reference WP_053025835.1, or homolog or functional fragment thereof.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds may exist in multiple crystalline or amorphous forms. In general, all physical forms are equivalent for the uses contemplated by the present disclosure and are intended to be within the scope of the present disclosure.

"Nucleic acid" refers to nucleotides (e.g., deoxyribonucleotides or ribonucleotides) and polymers thereof in either single-, double- or multiple-stranded form, or complements thereof; or nucleosides (e.g., deoxyribonucleosides or ribonucleosides). The term "nucleoside" refers, in the usual and customary sense, to a glycosylamine including a nucleobase and a five-carbon sugar (ribose or deoxyribose). Non limiting examples, of nucleosides include, cytidine, uridine, adenosine, guanosine, thymidine and inosine. The term "nucleotide" refers, in the usual and customary sense, to a single unit of a polynucleotide, i.e., a monomer. Nucleotides can be ribonucleotides, deoxyribonucleotides, or modified versions thereof.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amio acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

STING Agonists and Cyclic Dinucleotides

Provided herein are cyclic dinucleotides that are STING agonists. In aspects, the cyclic dincleotides comprise two purine bases or two modified purine bases in which the ribose sugars are bonded together via the phosphate or modified phosphate moiety. Exemplary purine bases include adenosine, guanosine, and inosine. In aspects, the phosphate or modified phosphate moiety is a monophosphate or modified monophosphate moiety.

The disclosure provides a STING agonist that is a compound of Formula (I), a stereoisomer of a compound of Formula (I), a pharmaceutically acceptable salt of a compound of Formula (I), or a pharmaceutically acceptable salt of a stereoisomer of a compound of Formula (I):

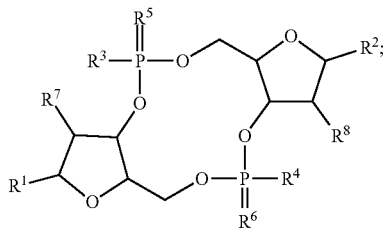

(I)

wherein $R^1$-$R^8$ are as defined herein. In embodiments, the disclosure provides a compound of Formula (I). In embodiments, the disclosure provides a stereoisomer of a compound of Formula (I). In embodiments, the disclosure provides a pharmaceutically acceptable salt of a compound of Formula (I). In embodiments, the disclosure provides a pharmaceutically acceptable salt of a stereoisomer of a compound of Formula (I).

The disclosure provides a STING agonist that is a compound of Formula (II), a stereoisomer of a compound of Formula (I), a pharmaceutically acceptable salt of a compound of Formula (II), or a pharmaceutically acceptable salt of a stereoisomer of a compound of Formula (II):

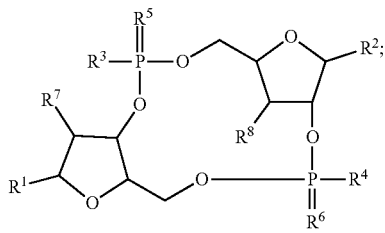

(II)

wherein $R^1$-$R^8$ are as defined herein. In embodiments, the disclosure provides a compound of Formula (II). In embodiments, the disclosure provides a stereoisomer of a compound of Formula (II). In embodiments, the disclosure provides a pharmaceutically acceptable salt of a compound of Formula (II). In embodiments, the disclosure provides a pharmaceutically acceptable salt of a stereoisomer of a compound of Formula (II).

The disclosure provides a STING agonist that is a compound of Formula (III), a stereoisomer of a compound of Formula (I), a pharmaceutically acceptable salt of a compound of Formula (III), or a pharmaceutically acceptable salt of a stereoisomer of a compound of Formula (III):

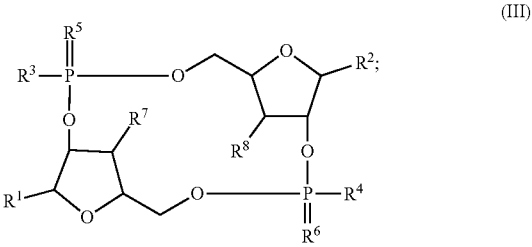

(III)

wherein $R^1$-$R^8$ are as defined herein. In embodiments, the disclosure provides a compound of Formula (III). In embodiments, the disclosure provides a stereoisomer of a compound of Formula (III). In embodiments, the disclosure provides a pharmaceutically acceptable salt of a compound of Formula (III). In embodiments, the disclosure provides a pharmaceutically acceptable salt of a stereoisomer of a compound of Formula (III).

In the compounds described herein, $R^1$ and $R^2$ are each independently G, tzG, thG, A, tzA, thA, X, tzX, or tzX. In embodiments, $R^1$ and $R^2$ are each independently G, tzG, thG, A, tzA, or thA, with the proviso that $R^1$ and $R^2$ are not both G and are not both A. In embodiments, $R^1$ and $R^2$ are each independently G, tzG, thG, A, tzA, thA, X, tzX, or thX, with the proviso that $R^1$ and $R^2$ are not both G, are not both A, and are not both X. In embodiments, $R^1$ and $R^2$ are each independently G, tzG, thG, or A. In embodiments, $R^1$ and $R^2$ are each independently G, tzG, thG, or A, with the proviso that $R^1$ and $R^2$ are not both G. In embodiments, $R^1$ and $R^2$ are each independently G, tzG, thG, or A, with the proviso that $R^1$ and $R^2$ are not both G and are not both A. In embodiments, $R^1$ and $R^2$ are each independently X, tzX, or thX. In embodiments, $R^1$ and $R^2$ are each independently X, tzX, or thX, with the proviso that $R^1$ and $R^2$ are not both X. In embodiments, $R^1$ and $R^2$ are each independently G, X, tzX, or thX. In embodiments, $R^1$ and $R^2$ are each independently G, X, tzX, or thX, with the proviso that $R^1$ and $R^2$ are not both X and are not both G. In embodiments, $R^1$ and $R^2$ are each independently G, tzX, or thX, with the proviso that $R^1$ and $R^2$ are not both G.

In embodiments, $R^1$ is G and $R^2$ is tzG. In embodiments, $R^1$ is tzG and $R^2$ is G. In embodiments, $R^1$ is G and $R^2$ is thG. In embodiments, $R^1$ is thG and $R^2$ is G. In embodiments, $R^1$ is A and $R^2$ is tzG. In embodiments, $R^1$ is tzG and $R^2$ is A. In embodiments, $R^1$ is A and $R^2$ is thG. In embodiments, $R^1$ is thG and $R^2$ is A. In embodiments, $R^1$ is A and $R^2$ is G. In embodiments, $R^1$ is G and $R^2$ is A. In embodiments, $R^1$ is tzG and $R^2$ is thG. In embodiments, $R^1$ is thG and $R^2$ is tzG. In embodiments, $R^1$ and $R^2$ are thG. In embodiments, $R^1$ and $R^2$ are tzG. In embodiments, $R^1$ and $R^2$ are A. In embodiments, $R^1$ and $R^2$ are G. In embodiments, $R^1$ and $R^2$ are thA. In embodiments, $R^1$ and $R^2$ are tzA. In embodiments, $R^1$ is G and $R^2$ is tzA. In embodiments, $R^1$ is G and $R^2$ is thA. In embodiments, $R^1$ is tzA and $R^2$ is G. In embodiments, $R^1$ is thA and $R^2$ is G. In embodiments, $R^1$ is A and $R^2$ is tzA. In embodiments, $R^1$ is A and $R^2$ is thA. In embodiments, $R^1$ is tzA and $R^2$ is A. In embodiments, $R^1$ is thA and $R^2$ is A. In embodiments, $R^1$ is X and $R^2$ is tzX. In embodiments, $R^1$ is tzX and $R^2$ is X. In embodiments, $R^1$ is X and $R^2$ is thX. In embodiments, $R^1$ is thX and $R^2$ is X. In embodiments, $R^1$ and $R^2$ are tzX. In embodiments, $R^1$ and $R^2$ are thX. In embodiments, $R^1$ is G and $R^2$ is tzX. In embodiments, $R^1$ is tzX and $R^2$ is G. In embodiments, $R^1$ is G and $R^2$ is thX. In embodiments, $R^1$ is thX and $R^2$ is G. In embodiments, $R^1$ is A and $R^2$ is tzX. In embodiments, $R^1$ is tzX and $R^2$ is A. In embodiments, $R^1$ is A and $R^2$ is thX. In embodiments, $R^1$ is thX and $R^2$ is A.

As used herein, "G" or "guanine moiety" is represented by the structure:

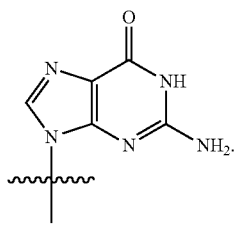 [SMILES: *n1cnc2c(=O)[nH]c(N)nc21]

As used herein, "tzG" or "$^{tz}$G" is represented by the structure:

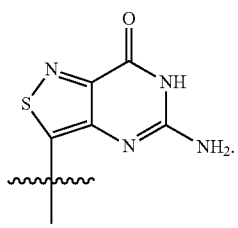 [SMILES: *c1snc2c(=O)[nH]c(N)nc12]

As used herein, "thG" or "$^{th}$G" is represented by the structure:

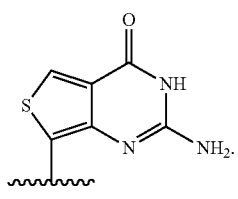 [SMILES: *c1scc2c(=O)[nH]c(N)nc12]

As used herein, "A" or "adenine moiety" is represented by the structure:

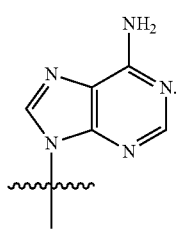 [SMILES: *n1cnc2c(N)ncnc21]

As used herein, "$^{tz}$A" or "tzA" is represented by the structure:

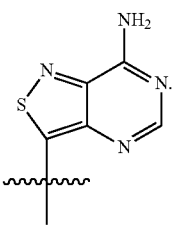 [SMILES: *c1snc2c(N)ncnc12]

As used herein, "$^{th}$A" or "thA" is represented by the structure:

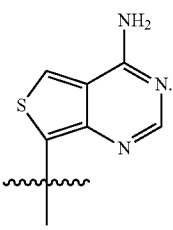 [SMILES: *c1scc2c(N)ncnc12]

As used herein, "X" or a "hypoxanthine moiety" is represented by the structure:

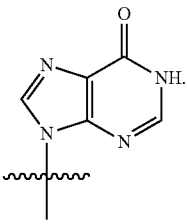 [SMILES: *n1cnc2c(=O)[nH]cnc21]

As used herein, "$^{tz}$X" or "tzX" is represented by the structure:

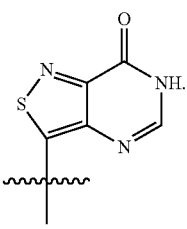 [SMILES: *c1snc2c(=O)[nH]cnc12]

As used herein, "$^{th}$X" or "thX" is represented by the structure:

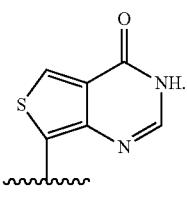 [SMILES: *c1scc2c(=O)[nH]cnc12]

In the compounds described herein, $R^3$ and $R^4$ are each independently —SH or —OH. In embodiments, $R^3$ and $R^4$ are —SH. In embodiments, $R^3$ and $R^4$ are —OH. In embodiments, $R^3$ is —SH and $R^4$ is —OH. In embodiments, $R^3$ is —OH and $R^4$ is —SH.

In the compounds described herein, $R^5$ and $R^6$ are each independently oxygen or sulfur. In embodiments, $R^5$ and $R^6$ are oxygen. In embodiments, $R^5$ and $R^6$ are sulfur. In embodiments, $R^5$ is oxygen and $R^6$ is sulfur. In embodiments, $R^5$ is sulfur and $R^6$ is oxygen.

In the compounds described herein, $R^7$ and $R^8$ are each independently halogen, hydrogen, —OH, or —OCH$_3$. In embodiments, $R^7$ and $R^8$ are each independently hydrogen, —OH, or —OCH$_3$. In embodiments, $R^7$ and $R^8$ are hydrogen. In embodiments, $R^7$ and $R^8$ are —OH. In embodiments, $R^7$ and $R^8$ are —OCH$_3$. In embodiments, one of $R^7$ and $R^8$ is hydrogen, and the other is —OH. In embodiments, one of $R^7$ and $R^8$ is hydrogen, and the other is —OCH$_3$. In embodiments, one of $R^7$ and $R^8$ is —OH, and the other is —OCH$_3$. In embodiments, one of $R^7$ and $R^8$ is halgoen, and the other is hydrogen, —OH, or —OCH$_3$. In embodiments, one of $R^7$ and $R^8$ is halgoen, and the other is —OH. In embodiments, halogen is Cl, F, Br, or I. In embodiments, halogen is Cl or F. In embodiments, halogen is F.

In embodiments, the stereoisomer of the compound of Formula (I) is a compound of Formula (IA):

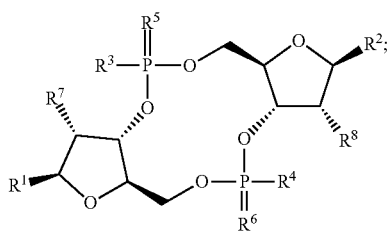

(IA)

wherein $R^1$-$R^8$ are as defined herein. In embodiments, the compound of Formula (I) is a compound of Formula (IA). In embodiments, the compound of Formula (I) is a pharmaceutically acceptable salt of the compound of Formula (IA).

In embodiments, the stereoisomer of the compound of Formula (I) is a compound of Formula (IB) or a pharmaceutically acceptable salt thereof:

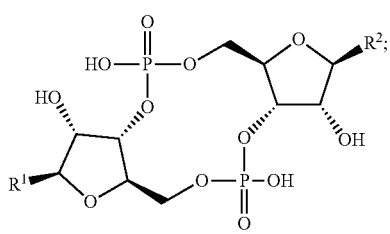

(IB)

wherein $R^1$ and $R^2$ are as set forth in Table A.

TABLE A

| Compound Name | $R^1$ | $R^2$ |
| --- | --- | --- |
| c-di-$^{tz}$GMP | $^{tz}$G | $^{tz}$G |
| c-di-$^{th}$GMP | $^{th}$G | $^{th}$G |
| c-G$^{th}$GMP | $^{th}$G | G |

TABLE A-continued

| Compound Name | $R^1$ | $R^2$ |
| --- | --- | --- |
| c-G$^{tz}$GMP | $^{tz}$G | G |
| c-GAMP | A | G |
| c-$^{th}$GMP | $^{th}$G | A |
| c-$^{tz}$GAMP | $^{tz}$G | A |
| c-G$^{th}$AMP | $^{th}$A | G |
| c-G$^{tz}$AMP | $^{tz}$A | G |
| c-di-$^{tz}$AMP | $^{tz}$A | $^{tz}$A |
| c-di-$^{th}$AMP | $^{th}$A | $^{th}$A |
| c-di-AMP | A | A |
| c-di-GMP | G | G |
| c-diXGMP | X | X |
| c-G$^{th}$XMP | $^{th}$X | G |
| c-G$^{tz}$XMP | $^{tz}$X | G |
| c-GXMP | X | G |
| c-AXMP | X | A |
| c-A$^{th}$XMP | $^{th}$X | A |
| c-A$^{tz}$XMP | $^{tz}$X | A |
| c-di-$^{th}$XMP | $^{th}$X | $^{th}$X |
| c-di-$^{tz}$XMP | $^{tz}$X | $^{tz}$X |

In embodiments, the compound of Formula (IB) is c-di$^{tz}$GMP, c-di-$^{th}$GMP, c-G$^{th}$GMP, c-G$^{tz}$GMP, c-GAMP, c-$^{th}$GMP, c-$^{tz}$GAMP, c-G$^{th}$AMP, c-G$^{tz}$AMP, c-di-$^{th}$AMP, c-di$^{tz}$AMP, c-di-AMP, c-di-GMP, c-diXGMP, c-G$^{th}$XMP, c-G$^{tz}$XMP, c-GXMP, c-AXMP, c-A$^{th}$XMP, c-A$^{tz}$XMP, c-di-$^{th}$XMP, or c-di$^{tz}$XMP. In embodiments, the compound of Formula (IB) is c-di$^{tz}$GMP, c-di-$^{th}$GMP, c-G$^{th}$GMP, c-G$^{tz}$GMP, c-GAMP, c-$^{th}$GMP, c-$^{tz}$GAMP, c-G$^{th}$AMP, c-di-$^{th}$AMP, c-di-$^{tz}$AMP, c-di-AMP, or c-G$^{th}$AMP. In embodiments, the compound of Formula (IB) is c-di-$^{tz}$GMP, c-di-$^{th}$GMP, c-G$^{th}$GMP, c-G$^{tz}$GMP, c-GAMP, c-$^{th}$GMP, c-$^{tz}$GAMP, c-G$^{th}$AMP, c-di-$^{th}$AMP, c-di-$^{tz}$AMP, or c-G$^{tz}$AMP. In embodiments, the compound of Formula (IB) is c-di-$^{tz}$GMP. In embodiments, the STING agonist is c-di-$^{th}$GMP. In embodiments, the compound of Formula (IB) is c-G$^{th}$GMP. In embodiments, the STING agonist is c-G$^{tz}$GMP. In embodiments, the compound of Formula (IB) is c-GAMP. In embodiments, the STING agonist is c-$^{th}$GMP. In embodiments, the compound of Formula (IB) is c-$^{tz}$GAMP. In embodiments, the compound of Formula (IB) is c-G$^{th}$AMP. In embodiments, the compound of Formula (IB) is c-G$^{tz}$AMP. In embodiments, the compound of Formula (IB) is c-di-$^{th}$AMP. In embodiments, the compound of Formula (IB) is c-di-$^{tz}$AMP. In embodiments, the compound of Formula (IB) is c-di-AMP. In embodiments, the compound of Formula (IB) is c-diXGMP. In embodiments, the compound of Formula (IB) is c-G$^{th}$XMP. In embodiments, the compound of Formula (IB) is c-G$^{tz}$XMP. In embodiments, the compound of Formula (IB) is c-GXMP. In embodiments, the compound of Formula (IB) is c-AXMP. In embodiments, the compound of Formula (IB) is c-A$^{th}$XMP. In embodiments, the compound of Formula (IB) is c-A$^{tz}$XMP. In embodiments, the compound of Formula (IB) is c-di-$^{th}$XMP. In embodiments, the compound of Formula (IB) is or c-di-$^{tz}$XMP.

In embodiments, the stereoisomer of the compound of Formula (II) is a compound of Formula (IIA):

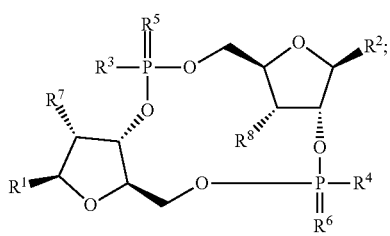

(IIA)

wherein $R^1$-$R^8$ are as defined herein. In embodiments, the compound of Formula (II) is a compound of Formula (IIA). In embodiments, the compound of Formula (II) is a pharmaceutically acceptable salt of the compound of Formula (IIA).

In embodiments, the stereoisomer of the compound of Formula (III) is a compound of Formula (IIIA):

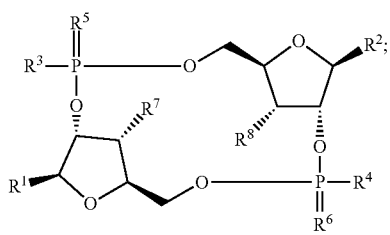

(IIIA)

wherein $R^1$-$R^8$ are as defined herein. In embodiments, the compound of Formula (III) is a compound of Formula (IIIA). In embodiments, the compound of Formula (III) is a pharmaceutically acceptable salt of the compound of Formula (IIIA).

The disclosure provides compounds of Formula (A) and Formula (B) that are the starting materials for the synthesis of the compounds described herein:

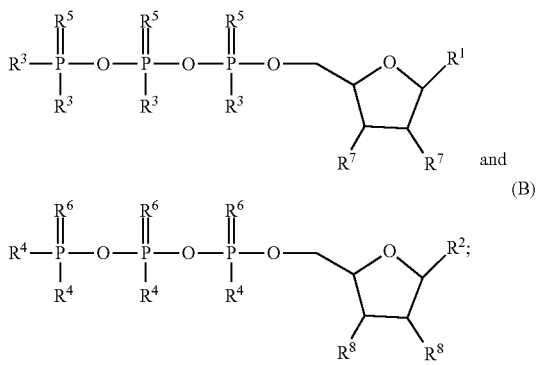

wherein $R^1$-$R^8$ are as defined herein. DncV is able to convert the compounds of Formula (A) and Formula (B) into the corresponding homo- and hetero-cyclic dinucleotides, e.g., the compounds of Formula (I), (II), or (III), including embodiments and aspects thereof. See, e.g., Li et al, Chem Eur J, 26:6076-6084 (2020), Novotna et al, J. Med. Chem., 62:10676-10690 (November 2019). In embodiments, the compounds described herein are made by a chemical synthetic process. The skilled artisan will appreciate how to make the compounds by chemical synthesis in view of the knowledge in the art. See, e.g., Ludford et al, ChemBioChem, 20:718-726 (February 2019); Kalia et al, Chem Soc Rev, 42:305-341 (2013).

Methods

The disclosure provides methods for increasing an immune response in a patient in need thereof by administering to the patient an effective amount of a STING agonist; a pharmaceutical composition comprising a STING agonist and a pharmaceutically acceptable excipient; or a vaccine comprising a STING agonist and an adjuvant. As described herein, the STING agonist is a compound of Formula (I); a compound of Formula (II); a compound of Formula (III); a stereoisomer of a compound of Formula (I); a compound of Formula (IA), a compound of Formula (IB), a compound of Formula (IIA), a compound of Formula (IIIA), a stereoisomer of a compound of Formula (II); a stereoisomer of a compound of Formula (III); a pharmaceutically acceptable salt of a compound of Formula (I); a pharmaceutically acceptable salt of a compound of Formula (II); a pharmaceutically acceptable salt of a compound of Formula (III); a pharmaceutically acceptable salt of a compound of Formula (IA), a pharmaceutically acceptable salt of a compound of Formula (IB), a pharmaceutically acceptable salt of a compound of Formula (IIA), a pharmaceutically acceptable salt of a compound of Formula (IIIA), a pharmaceutically acceptable salt of a stereoisomer of a compound of Formula (I); a pharmaceutically acceptable salt of a stereoisomer of a compound of Formula (II); or a pharmaceutically acceptable salt of a stereoisomer of a compound of Formula (III), including all embodiments and aspects of each of the foregoing.

The terms "immune response" and the like refer, in the usual and customary sense, to a response by an organism that protects against disease. The response can be mounted by the innate immune system or by the adaptive immune system, as well known in the art. The term "immune response" also encompasses, but is not limited to, an "adaptive immune response", also known as an "acquired immune response" in which adaptive immunity elicits immunological memory after an initial response to a specific pathogen or a specific type of cells that is targeted by the immune response, and leads to an enhanced response to that target on subsequent encounters. The induction of immunological memory can provide the basis of vaccination.

The term "increasing an immune response" and the like refer to an increase in the immune response of a subject as a consequence of administration of an agent, e.g., a compound as disclosed herein, including embodiments thereof. Accordingly, an immune response can be activated as a consequence of administration of an agent, e.g., a compound as disclosed herein, including embodiments thereof.

The term "immunogenic" or "antigenic" refers to a compound or composition described herein (including embodiments and aspects thereof) that induces an immune response, e.g., IFN, cytotoxic T lymphocyte (CTL) response, a B cell response (for example, production of antibodies that specifically bind the epitope), an NK cell response or any combinations thereof, when administered to a subject. Thus, an immunogenic or antigenic compound or composition is capable of eliciting an immune response in a subject.

The disclosure provides methods for treating cancer in a patient in need thereof, the method comprising administering to the patient an effective amount of a STING agonist; a pharmaceutical composition comprising a STING agonist and a pharmaceutically acceptable excipient, or a vaccine comprising a STING agonist and an adjuvant. In embodiments, the methods further comprise administering an effective amount of an anti-cancer agent (e.g., chemotherapeutic agent, checkpoint inhibitor) and/or radiation therapy. The disclosure provides methods for treating cancer in a patient in need thereof, the method comprising administering to the patient: (i) an effective amount of a STING agonist and an effective amount of a checkpoint inhibitor, (ii) an effective amount of a checkpoint inhibitor and an effective amount of a pharmaceutical composition comprising a STING agonist and a pharmaceutically acceptable excipient; (iii) an effective amount of a checkpoint inhibitor and an effective amount of a vaccine comprising a STING agonist and an adjuvant. In embodiments, the methods of treating cancer further comprise administering an effective amount of a checkpoint inhibitor to the patient to treat the cancer. As described herein, the STING agonist is a compound of Formula (I); a compound of Formula (II); a compound of Formula (III); a stereoisomer of a compound of Formula (I); a compound of Formula (IA), a compound of Formula (IB), a compound of Formula (IIA), a compound of Formula (IIIA), a stereoisomer of a compound of Formula (II); a stereoisomer of a compound of Formula (III); a pharmaceutically acceptable salt of a compound of Formula (I); a pharmaceutically acceptable salt of a compound of Formula (II); a pharmaceutically acceptable salt of a compound of Formula (III); a pharmaceutically acceptable salt of a compound of Formula (IA), a pharmaceutically acceptable salt of a compound of Formula (IB), a pharmaceutically acceptable salt of a compound of Formula (IIA), a pharmaceutically acceptable salt of a compound of Formula (IIIA), a pharmaceutically acceptable salt of a stereoisomer of a compound of Formula (I); a pharmaceutically acceptable salt of a stereoisomer of a compound of Formula (II); or a pharmaceutically acceptable salt of a stereoisomer of a compound of Formula (III), including all embodiments and aspects of each of the foregoing.

The term "cancer" refers to all types of cancer, neoplasm or malignant tumors found in mammals (e.g. humans), including leukemias, lymphomas, carcinomas and sarcomas. Exemplary cancers that may be treated with neural stem cells, vesicles, and pharmaceutical compositions described herein include brain cancer, glioma, glioblastoma, neuroblastoma, prostate cancer, colorectal cancer, pancreatic cancer, medulloblastoma, melanoma, cervical cancer, gastric cancer, ovarian cancer, lung cancer, cancer of the head, Hodgkin's disease, and Non-Hodgkin's lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer. In embodiments, the cancer is a solid tumor. In embodiments, the cancer is a metastatic solid tumor. In embodiments, the cancer is a lymphoma. In aspects, the cancer is a head and neck cancer. In embodiments, the cancer is breast cancer. In embodiments, the cancer is prostate cancer. In embodiments, the cancer is leukemia. In embodiments, the cancer is non-small cell lung cancer. In embodiments, the cancer is bladder cancer. In embodiments, the cancer is melanoma.

As used herein, the terms "metastasis," "metastatic," and "metastatic cancer" can be used interchangeably and refer to the spread of a proliferative disease or disorder, e.g., cancer, from one organ or another non-adjacent organ or body part. "Metastatic cancer" is also called "Stage IV cancer." Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

A "checkpoint inhibitor" or an "immune checkpoint inhibitor" as provided herein refers to a substance (e.g., an antibody or fragment thereof, a small molecule) that is capable of inhibiting, negatively affecting (e.g., decreasing) the activity or function of a checkpoint protein (e.g., decreasing expression or decreasing the activity of a checkpoint protein) relative to the activity or function of the checkpoint protein in the absence of the inhibitor. The checkpoint inhibitor may at least in part, partially or totally block stimulation, decrease, prevent, or delay activation, or inactivate, desensitize, or down-regulate signal transduction or enzymatic activity or the amount of a checkpoint protein. A checkpoint inhibitor may inhibit a checkpoint protein, e.g., by binding, partially or totally blocking, decreasing, preventing, delaying, inactivating, desensitizing, or down-regulating activity of the checkpoint protein. In embodiments, the checkpoint inhibitor is an antibody. In embodiments, the checkpoint inhibitor is an antibody fragment. In embodiments, the checkpoint inhibitor is an antibody variant. In embodiments, the checkpoint inhibitor is a scFv. In embodiments, the checkpoint inhibitor is an anti-CTLA-4 antibody. In embodiments, the checkpoint inhibitor is an anti-PD1 antibody. In embodiments, the checkpoint inhibitor is an anti-PD-L1 antibody. In embodiments, the checkpoint inhibitor is an anti-LAG-3 antibody. In embodiments, the checkpoint inhibitor is an anti-IgG1k antibody. In embodiments, the checkpoint inhibitor is an anti-CD25 antibody. In embodiments, the checkpoint inhibitor is an anti-IL2R antibody. In embodiments, the checkpoint inhibitor forms part of an oncolytic virus. Non-limiting examples of checkpoint inhibitors include ipilimumab, pembrolizumab, nivolumab, talimogene laherparepvec, durvalumab, daclizumab, avelumab, and atezolizumab.

The terms "immune checkpoint", "immune checkpoint protein" or "checkpoint protein" refer to compositions (molecules) capable of modulating the duration and amplitude of physiological immune responses (e.g., attenuate and/or eliminate sustained immune cell activation, hus regulating normal immune homeostasis). Immune checkpoint proteins may stimulate (increase) an immune response. In embodiments, the checkpoint protein is a cellular receptor. Examples, of stimulatory checkpoint molecules include, but are not limited to, members of the tumor necrosis factor (TNF) receptor superfamily (e.g. CD27, CD40, OX40, glucocorticoid-induced TNFR family related gene (GITR), and CD137), members of the B7-CD28 superfamily (e.g. CD28 itself and Inducible T-cell costimulator (ICOS)). Alternatively, immune checkpoint proteins may inhibit (decrease) an immune response. Examples of inhibitory checkpoint molecules include, but are not limited to, adenosine A2A receptor (A2AR), B7-H3, B7-H4, BTLA, CTLA-4, indoleamine 2,3-dioxygenase (IDO), killer immunoglobulin-like receptors (KIR), LAG3, PD-1, TIM-3, and V-domain immunoglobulin suppressor of T-cell activation (VISTA) protein.

An "anticancer agent" as used herein refers to a molecule (e.g. compound, peptide, protein, nucleic acid) used to treat cancer through destruction or inhibition of cancer cells or tissues. Anticancer agents may be selective for certain cancers or certain tissues.

"Anti-cancer agent" and "anticancer agent" are used in accordance with their plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate;

trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HC1), AC-7700 (Ajinomoto, i.e. AVE-8062, AVE-8062A, CS-39-L-Ser.HC1, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (-)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guúrin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), immunotherapy (e.g., cellular immunotherapy, antibody therapy, cytokine therapy, combination immunotherapy, etc.), radioimmunotherapy (e.g., anti-CD20 monoclonal antibody conjugated to $^{111}$In, $^{90}$Y, or $^{131}$I, etc.), immune checkpoint inhibitors (e.g., CTLA4 blockade, PD-1 inhibitors, PD-L1 inhibitors, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

The disclosure provides methods for treating an autoimmune disease in a patient in need thereof, the method comprising administering to the patient an effective amount of a STING agonist, pharmaceutical composition comprising a STING agonist and a pharmaceutically acceptable excipient, or a vaccine comprising a STING agonist and an adjuvant. As described herein, the STING agonist is a compound of Formula (I); a compound of Formula (II); a compound of Formula (III); a stereoisomer of a compound of Formula (I); a compound of Formula (IA), a compound of Formula (IB), a compound of Formula (IIA), a compound of Formula (IIIA), a stereoisomer of a compound of Formula (II); a stereoisomer of a compound of Formula (III); a pharmaceutically acceptable salt of a compound of Formula (I); a pharmaceutically acceptable salt of a compound of Formula (II); a pharmaceutically acceptable salt of a compound of Formula (III); a pharmaceutically acceptable salt of a compound of Formula (IA), a pharmaceutically acceptable salt of a compound of Formula (IB), a pharmaceutically acceptable salt of a compound of Formula (IIA), a pharmaceutically acceptable salt of a compound of Formula (IIIA), a pharmaceutically acceptable salt of a stereoisomer of a compound of Formula (I); a pharmaceutically acceptable salt of a stereoisomer of a compound of Formula (II); or a pharmaceutically acceptable salt of a stereoisomer of a compound of Formula (III), including all embodiments and aspects of each of the foregoing.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include acute Disseminated Encephalomyelitis (ADEM), acute necrotizing hemorrhagic leukoencephalitis, Addison's disease, agammaglobulinemia, alopecia areata, amyloidosis, ankylosing spondylitis, anti-GBM/Anti-TBM nephritis, antiphospholipid syndrome (APS), autoimmune angioedema, Autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticaria, axonal or neuronal neuropathies, Balo disease, Behcet's disease, bullous pemphigoid, cardiomyopathy, Castleman disease, celiac disease, Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogans syndrome, cold agglutinin disease, congenital heart block, coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, experimental allergic encephalomyelitis, evans syndrome, fibromyalgia, fibrosing alveolitis, giant cell arteritis (temporal arteritis), giant cell myocarditis, glomerulonephritis, goodpasture's syndrome, granulomatosis with polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, hypogammaglobulinemia, idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, microscopic polyangiitis, mixed connective tissue disease (MCTD), Mooren's ulcer, Mucha-Habermann disease, multiple sclerosis, myasthenia gravis, myositis, Narcolepsy, neuromyelitis optica (Devic's), Neutropenia, Ocular cicatricial pemphigoid, optic neuritis, palindromic rheumatism, PANDAS (Pediatric Autoimmune Neuropsychiatric Disorders Associated with Streptococcus), Paraneoplastic cerebellar degeneration, Paroxysmal nocturnal hemoglobinuria (PNH), parry Romberg syndrome, Parsonnage-Turner syndrome, Pars planitis (peripheral uveitis), Pemphigus, peripheral neuropathy, Perivenous encephalomyelitis, pernicious anemia, POEMS syndrome, polyarteritis nodosa, Type I, II, & III autoimmune polyglandular syndromes, polymyalgia rheumatica, polymyositis, Postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynauds phenomenon, reactive arthritis, Reflex sympathetic dystrophy, Reiter's syndrome, Relapsing polychondritis, restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, ulcerative colitis, undifferentiated connective tissue disease (UCTD), uveitis, vasculitis, vesiculobullous dermatosis, vitiligo, or Wegener's granulomatosis (i.e., granulomatosis with polyangiitis (GPA).

The disclosure provides methods for treating an inflammatory disease in a patient in need thereof, the method comprising administering to the patient an effective amount of a STING agonist, pharmaceutical composition comprising a STING agonist and a pharmaceutically acceptable excipient, or a vaccine comprising a STING agonist and an adjuvant. As described herein, the STING agonist is a compound of Formula (I); a compound of Formula (II); a compound of Formula (III); a stereoisomer of a compound of Formula (I); a compound of Formula (IA), a compound of Formula (IB), a compound of Formula (IIA), a compound of Formula (IIIA), a stereoisomer of a compound of Formula (II); a stereoisomer of a compound of Formula (III); a pharmaceutically acceptable salt of a compound of Formula (I); a pharmaceutically acceptable salt of a compound of Formula (II); a pharmaceutically acceptable salt of a compound of Formula (III); a pharmaceutically acceptable salt of a compound of Formula (IA), a pharmaceutically acceptable salt of a compound of Formula (IB), a pharmaceutically acceptable salt of a compound of Formula (IIA), a pharmaceutically acceptable salt of a compound of Formula (IIIA), a pharmaceutically acceptable salt of a stereoisomer of a compound of Formula (I); a pharmaceutically acceptable salt of a stereoisomer of a compound of Formula (II); or a pharmaceutically acceptable salt of a stereoisomer of a compound of Formula (III), including all embodiments and aspects of each of the foregoing.

The term "inflammatory disease" refers to a disease or condition characterized by aberrant inflammation (e.g. an increased level of inflammation compared to a control such as a healthy person not suffering from a disease). Examples of inflammatory diseases include enterocolitis (e.g., necrotizing enterocolitis), autoimmune diseases, arthritis, rheumatoid arthritis, psoriatic arthritis, juvenile idiopathic arthritis, multiple sclerosis, systemic lupus erythematosus, myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, Behcet's disease, Crohn's disease, ulcerative colitis, bullous pemphigoid, sarcoidosis, ichthyosis, Graves ophthalmopathy, inflammatory bowel disease, Addison's disease, vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis.

The disclosure provides methods for treating an infectious disease in a patient in need thereof, the method comprising administering to the patient an effective amount of a STING agonist, pharmaceutical composition comprising a STING agonist and a pharmaceutically acceptable excipient, or a vaccine comprising a STING agonist and an adjuvant. As described herein, the STING agonist is a compound of Formula (I); a compound of Formula (II); a compound of Formula (III); a stereoisomer of a compound of Formula (I);

a compound of Formula (IA), a compound of Formula (IB), a compound of Formula (IIA), a compound of Formula (IIIA), a stereoisomer of a compound of Formula (II); a stereoisomer of a compound of Formula (III); a pharmaceutically acceptable salt of a compound of Formula (I); a pharmaceutically acceptable salt of a compound of Formula (II); a pharmaceutically acceptable salt of a compound of Formula (III); a pharmaceutically acceptable salt of a compound of Formula (IA), a pharmaceutically acceptable salt of a compound of Formula (IB), a pharmaceutically acceptable salt of a compound of Formula (IIA), a pharmaceutically acceptable salt of a compound of Formula (IIIA), a pharmaceutically acceptable salt of a stereoisomer of a compound of Formula (I); a pharmaceutically acceptable salt of a stereoisomer of a compound of Formula (II); or a pharmaceutically acceptable salt of a stereoisomer of a compound of Formula (III), including all embodiments and aspects of each of the foregoing.

The term "infection" or "infectious disease" refers to a disease or condition that can be caused by organisms such as a bacterium, virus, fungi or any other pathogenic microbial agents. In embodiments, the infectious disease is caused by a pathogenic bacteria. Pathogenic bacteria are bacteria which cause diseases (e.g., in humans). In embodiments, the infectious disease is a bacteria associated disease (e.g., tuberculosis, which is caused by Mycobacterium tuberculosis). Non-limiting bacteria associated diseases include pneumonia, which may be caused by bacteria such as Streptococcus and Pseudomonas; or foodborne illnesses, which can be caused by bacteria such as Shigella, Campylobacter, and Salmonella. Bacteria associated diseases also includes tetanus, typhoid fever, diphtheria, syphilis, and leprosy. In embodiments, the disease is Bacterial vaginosis (i.e. bacteria that change the vaginal microbiota caused by an overgrowth of bacteria that crowd out the Lactobacilli species that maintain healthy vaginal microbial populations) (e.g., yeast infection, or Trichomonas vaginalis); Bacterial meningitis (i.e. a bacterial inflammation of the meninges); Bacterial pneumonia (i.e. a bacterial infection of the lungs); Urinary tract infection; Bacterial gastroenteritis; or Bacterial skin infections (e.g. impetigo, or cellulitis). In embodiments, the infectious disease is a *Campylobacter jejuni, Enterococcus faecalis, Haemophilus influenzae, Helicobacter pylori, Klebsiella pneumoniae, Legionella pneumophila, Neisseria gonorrhoeae, Neisseria meningitides, Staphylococcus aureus, Streptococcus pneumonia*, or *Vibrio cholera* infection.

The disclosure provides methods for treating a viral disease in a patient in need thereof, the method comprising administering to the patient an effective amount of a STING agonist, pharmaceutical composition comprising a STING agonist and a pharmaceutically acceptable excipient, or a vaccine comprising a STING agonist and an adjuvant. As described herein, the STING agonist is a compound of Formula (I); a compound of Formula (II); a compound of Formula (III); a stereoisomer of a compound of Formula (I); a compound of Formula (IA), a compound of Formula (IB), a compound of Formula (IIA), a compound of Formula (IIIA), a stereoisomer of a compound of Formula (II); a stereoisomer of a compound of Formula (III); a pharmaceutically acceptable salt of a compound of Formula (I); a pharmaceutically acceptable salt of a compound of Formula (II); a pharmaceutically acceptable salt of a compound of Formula (III); a pharmaceutically acceptable salt of a compound of Formula (IA), a pharmaceutically acceptable salt of a compound of Formula (IB), a pharmaceutically acceptable salt of a compound of Formula (IIA), a pharmaceutically acceptable salt of a compound of Formula (IIIA), a pharmaceutically acceptable salt of a stereoisomer of a compound of Formula (I); a pharmaceutically acceptable salt of a stereoisomer of a compound of Formula (II); or a pharmaceutically acceptable salt of a stereoisomer of a compound of Formula (III), including all embodiments and aspects of each of the foregoing.

The term "viral infection" or "viral disease" refers to a disease or condition that is caused by a virus. Non-limiting examples of viral infections include hepatic viral diseases (e.g., hepatitis A, B, C, D, E), herpes virus infection (e.g., HSV-1, HSV-2, herpes zoster), flavivirus infection, Zika virus infection, cytomegalovirus infection, a respiratory viral infection (e.g., adenovirus infection, influenza, severe acute respiratory syndrome, coronavirus infection (e.g., SARS-CoV-1, SARS-CoV-2, MERS-CoV, COVID-19, MERS)), a gastrointestinal viral infection (e.g., norovirus infection, rotavirus infection, astrovirus infection), an exanthematous viral infection (e.g., measles, shingles, smallpox, rubella), viral hemorrhagic disease (e.g., Ebola, Lassa fever, dengue fever, yellow fever), a neurologic viral infection (e.g., West Nile viral infection, polio, viral meningitis, viral encephalitis, Japanese encephalitis, rabies), and human papilloma viral infection. In embodiments, the viral infection is a coronavirus infection. In embodiments, the viral infection is SARS-CoV-1. In embodiments, the viral infection is SARS-CoV-2. In embodiments, the viral infection is MERS-CoV. In embodiments, the viral disease is COVID-19. In embodiments, the viral disease is MERS (Middle Eastern respiratory syndrome).

The disclosure provides methods for activating a STING protein, the method comprising contacting the STING protein with an effective amount of a STING agonist, pharmaceutical composition comprising a STING agonist and a pharmaceutically acceptable excipient, or a vaccine comprising a STING agonist and an adjuvant. As described herein, the STING agonist is a compound of Formula (I); a compound of Formula (II); a compound of Formula (III); a stereoisomer of a compound of Formula (I); a compound of Formula (IA), a compound of Formula (IB), a compound of Formula (IIA), a compound of Formula (IIIA), a stereoisomer of a compound of Formula (II); a stereoisomer of a compound of Formula (III); a pharmaceutically acceptable salt of a compound of Formula (I); a pharmaceutically acceptable salt of a compound of Formula (II); a pharmaceutically acceptable salt of a compound of Formula (III); a pharmaceutically acceptable salt of a compound of Formula (IA), a pharmaceutically acceptable salt of a compound of Formula (IB), a pharmaceutically acceptable salt of a compound of Formula (IIA), a pharmaceutically acceptable salt of a compound of Formula (IIIA), a pharmaceutically acceptable salt of a stereoisomer of a compound of Formula (I); a pharmaceutically acceptable salt of a stereoisomer of a compound of Formula (II); or a pharmaceutically acceptable salt of a stereoisomer of a compound of Formula (III), including all embodiments and aspects of each of the foregoing.

As defined herein, the term "activation", "activate", "activating", "activator" and the like in reference to a protein-inhibitor interaction means positively affecting (e.g. increasing) the activity or function of the protein relative to the activity or function of the protein in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In aspects, treating is preventing. In aspects, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In embodiments, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, and other non-mammalian animals. In embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

Pharmaceutical Compositions

The disclosure provides pharmaceutical compositions comprising a pharmaceutically acceptable excipient and a STING agonist. As described herein, the STING agonist is a compound of Formula (I); a compound of Formula (II); a compound of Formula (III); a stereoisomer of a compound of Formula (I); a compound of Formula (IA), a compound of Formula (IB), a compound of Formula (IIA), a compound of Formula (IIIA), a stereoisomer of a compound of Formula (II); a stereoisomer of a compound of Formula (III); a pharmaceutically acceptable salt of a compound of Formula (I); a pharmaceutically acceptable salt of a compound of Formula (II); a pharmaceutically acceptable salt of a compound of Formula (III); a pharmaceutically acceptable salt of a compound of Formula (IA), a pharmaceutically acceptable salt of a compound of Formula (IB), a pharmaceutically acceptable salt of a compound of Formula (IIA), a pharmaceutically acceptable salt of a compound of Formula (IIIA), a pharmaceutically acceptable salt of a stereoisomer of a compound of Formula (I); a pharmaceutically acceptable salt of a stereoisomer of a compound of Formula (II); or a pharmaceutically acceptable salt of a stereoisomer of a compound of Formula (III), including all embodiments and aspects of each of the foregoing.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

Pharmaceutical compositions can be administered for therapeutic or prophylactic treatments. In therapeutic applications, compositions are administered to a patient suffering from a disease (e.g., cancer) in a "therapeutically effective dose." Amounts effective for this use will depend upon the severity of the disease and the general state of the patient's health. Single or multiple administrations of the compositions may be administered depending on the dosage and frequency as required and tolerated by the patient.

Pharmaceutical compositions provided herein include compositions wherein the active ingredient (e.g. compositions described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, the compounds described herein will contain an amount of active ingredient effective to achieve the desired result, e.g., modulating the activity of a target molecule, and/or reducing, eliminating, or slowing the progression of disease symptoms. Determination of a therapeutically effective amount of a compound described herein is well within the capabilities of those skilled in the art, especially in light of the detailed disclosure herein.

Pharmaceutical compositions can include a single agent or more than one agent. The Pharmaceutical compositions for administration will commonly include an agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary, and will be selected primarily based on fluid volumes, viscosities, body weight and the like in accordance with the particular mode of administration selected and the subject's needs.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In aspects, oral pharmaceutical compositions will comprise an inert diluent or edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 1 to about 90% of the weight of the unit, or preferably between 1-60%. The amount of active compounds in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the active compounds in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The Pharmaceutical compositions of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

Vaccines

The pharmaceutical compositions described herein may be in the form of a vaccine when they are intended to be administered to a subject for the purpose of generating antibodies and/or treating or preventing a disease, such as cancer.

In aspects, the disclosure provides a vaccine comprising a STING agonist and an adjuvant. In aspects, the disclosure provides a vaccine comprising a STING agonist, a pharmaceutically acceptable excipient, and an adjuvant. The vaccines may comprise any pharmaceutically acceptable adjuvants known in the art, such as those described herein. As described herein, the STING agonist is a compound of Formula (I); a compound of Formula (II); a compound of Formula (III); a stereoisomer of a compound of Formula (I); a compound of Formula (IA), a compound of Formula (IB), a compound of Formula (IIA), a compound of Formula (IIIA), a stereoisomer of a compound of Formula (II); a stereoisomer of a compound of Formula (III); a pharmaceutically acceptable salt of a compound of Formula (I); a pharmaceutically acceptable salt of a compound of Formula (II); a pharmaceutically acceptable salt of a compound of Formula (III); a pharmaceutically acceptable salt of a compound of Formula (IA), a pharmaceutically acceptable salt of a compound of Formula (IB), a pharmaceutically acceptable salt of a compound of Formula (IIA), a pharmaceutically acceptable salt of a compound of Formula (IIIA), a pharmaceutically acceptable salt of a stereoisomer of a compound of Formula (I); a pharmaceutically acceptable salt of a stereoisomer of a compound of Formula (II); or a pharmaceutically acceptable salt of a stereoisomer of a compound of Formula (III), including all embodiments and aspects of each of the foregoing.

The term "vaccine" refers to a composition that can provide active acquired immunity to and/or therapeutic effect (e.g. treatment) of a particular disease or a pathogen. A vaccine typically contains one or more agents that can induce an immune response in a subject against a pathogen or disease, i.e. a target pathogen or disease. The immunogenic agent stimulates the body's immune system to recognize the agent as a threat or indication of the presence of the target pathogen or disease, thereby inducing immunological memory so that the immune system can more easily recognize and destroy any of the pathogen on subsequent exposure. Vaccines can be prophylactic (e.g. preventing or ameliorating the effects of a future infection by any natural or pathogen, or of an anticipated occurrence of cancer in a predisposed subject) or therapeutic (e.g., treating cancer in a subject who has been diagnosed with the cancer). The administration of vaccines is referred to vaccination. In embodiments, a vaccine composition can provide any of the compounds described herein (including embodiments and aspects thereof).

In aspects, the adjuvant comprises an aluminum salt. In embodiments, the aluminum salt is aluminum sulfate, aluminum phosphate, aluminum hydroxyphosphate, aluminum hydroxide, potassium aluminum sulfate, or a combination of two or more thereof. In embodiments, the aluminum salt is aluminum sulfate. In embodiments, the aluminum salt is aluminum phosphate. In embodiments, the aluminum salt is aluminum hydroxyphosphate. In embodiments, the aluminum salt is aluminum hydroxide. In embodiments, the aluminum salt is potassium aluminum sulfate.

In aspects, the adjuvant comprises a toll-like receptor agonist. In embodiments, the toll-like receptor is toll-like receptor 2 agonist, toll-like receptor 3 agonist, toll-like receptor 4 agonist, toll-like receptor 5 agonist, toll-like receptor 7 agonist, toll-like receptor 8 agonist, toll-like receptor 9 agonist, or a combination of two or more thereof. In embodiments, the toll-like receptor agonist is toll-like receptor 3 agonist. In embodiments, the toll-like receptor agonist is toll-like receptor 9 agonist. In embodiments, the toll-like receptor 9 agonist is a CpG ODN. In embodiments, the CpG ODN is a CpG-A ODN, a CpG-B ODN, a CpG-C ODN, or a combination of two or more thereof.

In aspects, the adjuvant comprises an aluminum salt and a toll-like receptor agonist. In embodiments, the aluminum salt is aluminum sulfate, aluminum phosphate, aluminum hydroxyphosphate, aluminum hydroxide, potassium aluminum sulfate, or a combination of two or more thereof. In embodiments, the aluminum salt is aluminum sulfate. In embodiments, the aluminum salt is aluminum phosphate. In embodiments, the aluminum salt is aluminum hydroxyphosphate. In embodiments, the aluminum salt is aluminum hydroxide. In embodiments, the aluminum salt is potassium aluminum sulfate. In embodiments, the toll-like receptor is toll-like receptor 2 agonist, toll-like receptor 3 agonist, toll-like receptor 4 agonist, toll-like receptor 5 agonist, toll-like receptor 7 agonist, toll-like receptor 8 agonist, toll-like receptor 9 agonist, or a combination of two or more thereof. In embodiments, the toll-like receptor agonist is toll-like receptor 3 agonist. In embodiments, the toll-like receptor agonist is toll-like receptor 9 agonist. In embodiments, the toll-like receptor 9 agonist is a CpG ODN. In embodiments, the CpG ODN is a CpG-A ODN, a CpG-B ODN, a CpG-C ODN, or a combination of two or more thereof.

In aspects, the adjuvant comprises a surfactant (e.g., hexadecylamine, octadecylamine, lysolecithin, dimethyldioctadecylammonium bromide, N,N-dioctadecyl-N',N-bis (2-hydroxy-ethylpropane diamine), methoxyhexadecyl glycerol, pluronic polyols); polyanions (e.g., pyran, dextran sulfate, poly IC, polyacrylic acid, Carbopol); peptides (e.g., muramyl dipeptide, aimethylglycine), tuftsin, oil emulsions, B peptide subunits of *E. coli*, or a combination of two or more thereof. In embodiments, the adjuvant comprises a surfactant.

The vaccines and pharmaceutical compositions may be lyophilized or in aqueous form, i.e., solutions or suspensions. Liquid formulations allow the vaccines or pharmaceutical compositions to be administered direct from their packaged form, without the need for reconstitution in an aqueous medium, and are thus ideal for injection. Vaccines and pharmaceutical compositions may be presented in vials, or they may be presented in ready filled syringes. The syringes may be supplied with or without needles. A syringe will include a single dose of the composition, whereas a vial may include a single dose or multiple doses (e.g. 2, 3, or 4 doses). In embodiments, the dose is for a human and may be administered by injection.

Liquid vaccines are also suitable for reconstituting other vaccines from a lyophilized form. Where a vaccine is to be used for such extemporaneous reconstitution, the disclosure provides a kit, which may comprise two vials, or may comprise one ready-filled syringe and one vial, with the contents of the syringe being used to reconstitute the contents of the vial prior to injection. Vaccines may be packaged in unit dose form or in multiple dose form (e.g. 2, 3, or 4 doses). For multiple dose forms, vials can be pre-filled syringes. Effective dosage volumes can be routinely established, but a typical human dose of the composition has an injection volume of 0.25 to 1 mL.

In embodiments, vaccines have a pH of between 6.0 and 8.0, and may be buffered at this pH. Stable pH may be maintained by the use of a buffer, such as a phosphate buffer or a histidine buffer. The composition should be sterile and/or pyrogen free. The compositions and vaccines may be isotonic. Vaccines may include an antimicrobial, particularly when packaged in a multiple dose format. Other antimicrobials may be used, such as 2-phenoxyethanol or parabens (methyl, ethyl, propyl parabens). Preservative may be added exogenously and/or may be a component of the bulk haptens or hapten conjugates which are mixed to form the composition (e.g. present as a preservative in pertussis antigens). Vaccines may comprise detergent e.g. a Tween (polysorbate), such as Tween 80. Detergents are generally present at low levels, e.g. <0.01%. Vaccines may include sodium salts (e.g. sodium chloride) to give tonicity.

Dosages

The dosage and frequency (single or multiple doses) of the compounds, pharmaceutical compositions, or vaccines administered to a subject can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer and severity of such symptoms), kind of concurrent treatment, complications from the disease being treated or other health-related problems. Other therapeutic regimens or agents can be used in conjunction with the methods, compounds, pharmaceutical compositions, and vaccines described herein. Adjustment and manipulation of established dosages (e.g., frequency and duration) are well within the ability of those skilled in the art.

For any compound, pharmaceutical composition, or vaccines described herein, the therapeutically effective amount can be initially determined from cell culture assays. Target concentrations will be those concentrations of compounds, pharmaceutical compositions, or vaccines that are capable of achieving the methods described herein, as measured using the methods described herein or known in the art. As is well known in the art, effective amounts of compounds, pharmaceutical compositions, or vaccines for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages of the compounds, pharmaceutical compositions, or vaccines may be varied depending upon the requirements of the patient. The dose administered to a patient should be sufficient to affect a beneficial therapeutic response in the patient over time. The size of the dose also will be determined by the existence, nature, and extent of any adverse side-effects. Determination of the proper dosage for a particular situation is within the skill of the art. Generally, treatment is initiated with smaller dosages which are less than the optimum dose of the compounds, pharmaceutical compositions, or vaccines. Thereafter, the dosage is increased by small increments until the optimum effect under circumstances is reached. Dosage amounts and intervals can be adjusted individually to provide levels of the compounds, pharmaceutical compositions, or vaccines effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the choice of compounds, pharmaceutical compositions, or vaccines by considering factors such as compound potency, relative bioavailability, patient body weight, presence and severity of adverse side effects.

EXAMPLES

The following examples are for purposes of illustration only and are not intended to limit the spirit or scope of the claims.

The discovery that cyclic dinucleotides (CDNs), bacterial second messengers, trigger the innate immune response in eukaryotic cells through the STING-TBK1 pathway has provided new insight into their biology and applications. Described herein is the enzymatic preparation, as well as biophysical and biochemical application of a novel group of c-di-GMP analogs. By employing an "atomic mutagenesis" strategy, which allowed the inventors to change one specific atom in a molecule at a time, valuable mechanistic insights into reactions mediated by cyclase and phosphodiesterase (PDE), which play important roles in c-di-GMP metabolism and signaling transduction, were obtained. Moreover, these c-di-GMP analogs that featured a gradual change in their atomic structures display variations in their ability to induce type-I interferon (IFN) production, with several derivatives being more potent than their native archetype.

Cyclic dinucleotides activate the innate immune response through the STING-TBK1 pathway in mammalian cells. When transfected into mammalian cells, the compounds bind and activate STING, an important protein of the innate immune system. When activated, STING promotes the production of multiple types of cytokines and interferons by activating transcription regulation factors like IRF3 and STAT6. Applicant has demonstrated that the compounds induced interferon production in transfected RAW 264.7 cells.

Synthesized from modified ribonucleoside triphosphates, the compounds described herein are surrogates of the native STING ligands, cyclic dinucleotides (CDNs). Different from most of the existing CDN derivatives, where the modification were carried by the phosphodiester bonds, the present CDN derivatives feature modified nucleobases. The present CDN derivatives also demonstrate high potency in activating STING. The interferon production induced by one of the present CDN derivatives was 10-fold higher than that of the native CDN. The CDN derivatives with modified nucleobases demonstrate higher potency in inducing interferon production than their native archetype.

Example 1

The dimeric and mixed CDN analogues described herein (e.g., c-di-$^{tz}$GMP, c-di-$^{th}$GMP, c-G$^{th}$GMP, c-G$^{tz}$GMP, c-GAMP, c-$^{th}$GMP, c-di-GMP) were made from G, thG, or tzG by using DncV, a promiscuous dinucleotide cyclase from *Vibrio cholerae*. More particularly, guanosine 5'-triphosphates analogs (G, thGTP, tzGTP) (500 µM) [or adensone 5'-triphosphate analogs (A, thA, tzA) (500 µM)] were incubated with DncV (2.3 µM) in a buffer (0.1 M NaCl, 40 mM Tris pH 7.5 and 10 mM MgCl$_2$) at 37° C. for 2-5 h, or room temperature overnight. The reaction mixture was then heated at 90° C. for 5 min and chilled on ice for 15 minutes and filtered through a 0.22 µm filter. The supernatant was separated by Sepax Bio C-18 column (250×10 mm, 5 µm particle size) with a gradient of 0.5-20% of 10 mM NH4OAc, pH 7 in MeOH in 20 minutes on an Agilent 1200 or 1260 series HPLC system (Agilent Technologies). Collected HPLC fractions were lyophilized with Labconco FreeZone 2.5 lyophilizer and re-dissolved in autoclaved water. UV spectroscopy was used to determine the concentration of each solution with the following extinction coefficients: 26000 L mol-1 cm-1 for c-di-GMP (260 nm), 8370 L mol-1 cm-1 for c-di-tzGMP (333 nm), 7470 L mol-1 cm-1 for c-dithGMP (321 nm), 3735 L mol-1 cm-1 for c-GthGMP (333 nm), and 4185 L mol-1 cm-1 for c-GtzGMP (333 nm). See Li, Ludford, Fin, Rovira, and Tor, "Enzymatic Syntheses and Applications of Fluorescent Cyclic Dinucleotides," Chem. Eur. J., Vol. 26, Issue 27 (March 2020).

The dimeric and mixed adenine analogues described herein (e.g., c-$^{tz}$GAMP, c-G$^{th}$AMP, c-G$^{tz}$AMP, c-di-$^{th}$AMP, c-di-$^{tz}$AMP, c-di-AMP, c-di-GMP) were made from A, thA, and tzA following the methods described in the preceding paragraph. HR-ESI-TOFMS of c-di-$^{th}$AMP: calculated for [C$_{22}$H$_{23}$N$_6$O$_{12}$P$_2$S$_2$]$^-$, 689.0296. Found 689.0284, delta (ppm) −1.7. Sample was dissolved in autoclaved water and spectrum was obtained on an Agilent 6230 HR-ESI-TOF MS. HR-ESI-TOFMS of c-A$^{th}$AMP: calculated for [C$_{21}$H$_{23}$N$_8$O$_{12}$P$_2$S]$^-$, 673.0637. Found 673.0629, delta (ppm) −1.2. Sample was dissolved in autoclaved water and spectrum was obtained on an Agilent 6230 HR-ESI-TOF MS. HR-ESI-TOFMS of c-di-$^{tz}$AMP: calculated for [C$_{20}$H$_{21}$N$_8$O$_{12}$P$_2$S$_2$]$^-$, 691.0201. Found 691.0194, delta (ppm) −1.0. Sample was dissolved in autoclaved water and spectrum was obtained on an Agilent 6230 HR-ESI-TOF MS. HR-ESI-TOFMS of c-G$^{th}$AMP: calculated for [C$_{21}$H$_{23}$N$_8$O$_{13}$P$_2$S]$^-$, 689.0586. Found 689.0578, delta (ppm) −1.2. Sample was dissolved in autoclaved water and spectrum was obtained on an Agilent 6230 HR-ESI-TOF MS. HR-ESI-TOFMS of c-G$^{tz}$AMP: calculated for [C$_{20}$H$_{22}$N$_9$O$_{13}$P$_2$S]$^-$, 690.0538. Found 690.0534, delta (ppm) −0.6. Sample was dissolved in autoclaved water and spectrum was obtained on an Agilent 6230 HR-ESI-TOF MS.

Example 2

The inventors analyzed the immunostimulatory effects of the CDNs described herein, and demonstrate herein that certain analogues induced type-I IFN production more potently than their native archetype, highlighting the ability of the compounds to manipulate the eukaryotic innate immune response. Shin, Sinkeldam, and Tor, J. Am. Chem. Soc. 2011, 133, 14912-14915; Rovira, Fin, and Tor, J. Am. Chem. Soc. 2015, 137, 14602-14605; Li, Ludford, Fin, Rovira, and Tor, Chem. Eur. J. 2020, 27, 6076-6084.

To preliminarily determine whether the synthetic c-di-GMP analogues could activate the IFN response in eukaryotic cells, THP-1 cells were treated with 5 μM of c-di-GMP, c-GthGMP and c-di-thGMP. After 4 h incubation, induction of type-I IFN was measured with HEK-Blue IFN α/β reporter cells. c-GthGMP induced type-I IFN production with comparable efficiency to cdi-GMP, while c-di-thGMP showed no activity (FIG. 1).

Figure 2A:
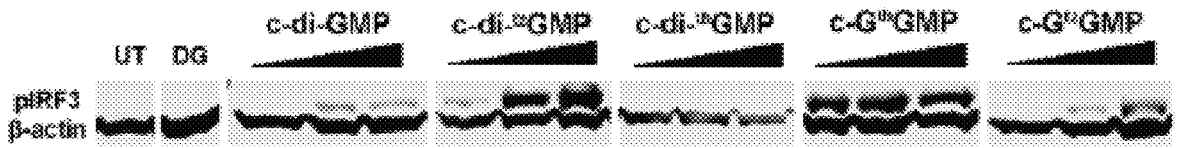
FIGS. 2A-2B show IRF3 phosphorylation induced by c-di-GMP and its analogues.
Figure 2B:
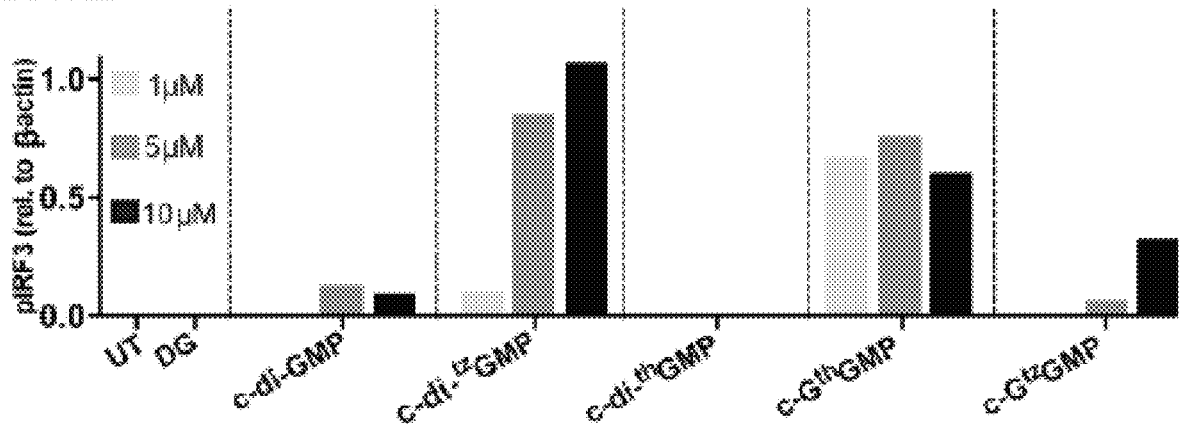

To analyze the immunostimulatory effects of all synthetic CDNs in greater detail, RAW 264.7 cells were treated with various concentrations of c-di-GMP, c-di-tzGMP, c-di-thGMP, c-GthGMP and c-GtzGMP and the phosphorylation of IRF3 to pIRF3 was evaluated. CDNs were thus transfected into RAW 264.7 murine cells with digitonin as described in previous studies.[7b,16] Cells were then lysed with NP-40 buffer 2 h after transfection, and total protein was collected for immunoblotting against phosphorylated IRF3 (pIRF3) and β-actin. No pIRF3 was observed for untreated cells (UT) or digitonin-permeabilized cells (DG; FIGS. 2A-2B). Low concentrations (1 μM) of c-di-GMP did not induce obvious IRF3 activation, while 5 and 10 μM displayed comparable efficiency in inducing IRF3 phosphorylation. Increasing amounts of phosphorylated IRF3 were observed when cells were treated with higher concentrations of c-di-tzGMP and c-GtzGMP, while no clear dose-response was observed for c-GthGMP (FIGS. 2A-2B). The least isomorphic analogue, c-di-thGMP, did not trigger observable IRF3 activation at any of the concentrations tested. Two other biological replicates produced similar trends (See FIG. S2 in Yi et al, ChemBioChem, Volume 21 (2020)).

Figure 3A:
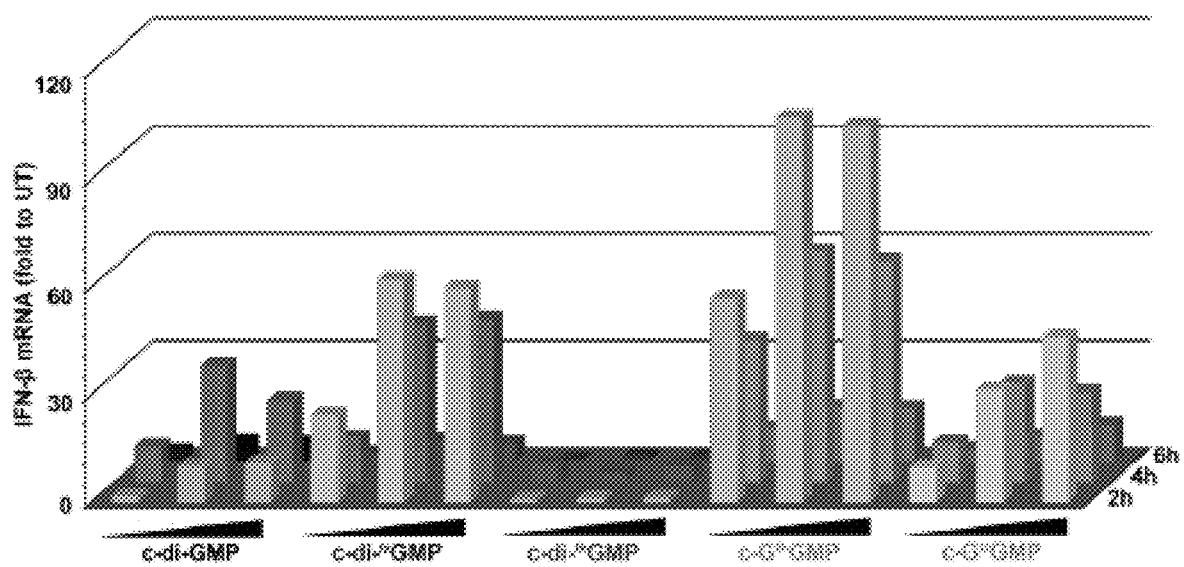
FIGS. 3A-3C provide IFN data.
Figure 3B:
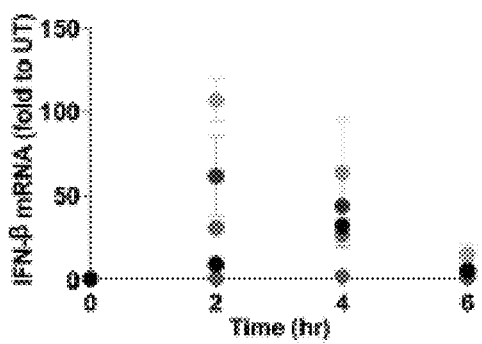
Figure 3C:
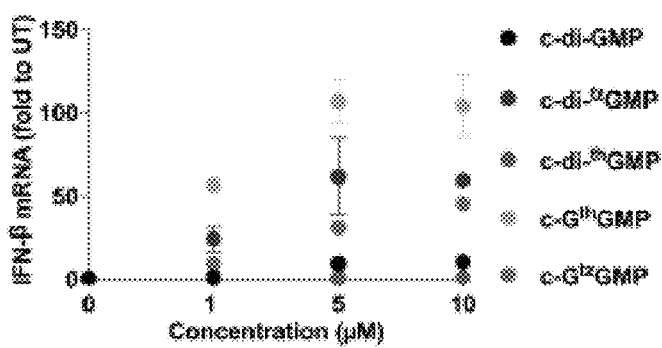

As most synthetic c-di-GMP analogues activated IRF3, the inventors analyzed their dose and time dependency for inducing IFN-β mRNA production by using RT-qPCR. RAW 264.7 cells were transfected with 1, 5 and 10 μM of CDNs as described above and incubated for 2, 4 and 6 h. Total RNA was isolated and used for RT-qPCR. As shown in FIGS. 3A-3B, c-di-GMP induced the most IFN-β mRNA production 4 h post transfection, whereas the highest response was observed after 2 h for c-di-tzGMP, c-GthGMP, and c-GtzGMP. The same trend was observed for all three concentrations of CDNs tested (FIG. 3A; see also Figures. S3a,b in Yi et al, ChemBioChem, Volume 21 (2020)). The IFN response to c-di-thGMP was minimal, but c-GthGMP showed the highest potency in inducing IFN-β mRNA production (FIGS. 3A-3C; see also Figures S3a-d in Yi et al, ChemBioChem, Volume 21 (2020)) among all CDNs tested. After 2 h of incubation, 5 μM of c-GthGMP induced tenfold higher IFN-β mRNA production than c-di-GMP, the native messenger. The differences in activity displayed by the analogues and their dependency on the specific assay used are discussed below.

Apparent STING activation by c-di-GMP analogues that contain unnatural isomorphic nucleobases was assessed here by three methods: type I IFN production measured by a reporter cell line, IRF3 phosphorylation measured by western blotting, and IFN-β mRNA production measured by RT-qPCR. The initial analysis was performed in THP-1, a human cell line, whereas more detailed analyses were performed in RAW 264.7, a murine cell line. The results show that all analogues except for cdi-thGMP stimulated the STING pathway in RAW 264.7 cells. The other three analogues stimulated IRF phosphorylation at comparable or higher levels than the parent c-di-GMP 2 h post transfection.

To quantitatively analyze activation of the STING pathway, CDN-induced, IFN-β production was measured by RT-qPCR in time- and dose-dependent manners. As seen in FIG. 3, IFN-β induction drops in the order: c-GthGMP>c-di-tzGMP>c-GtzGMP>c-di-GMP>c-di-thGMP, although it is apparent the cellular processes show complex concentration/time dependency. The effect of CDN concentrations above 5 μM plateaued except for c-GtzGMP. Importantly, however, peak IFN-β responses occurred at different times for different analogues, with the synthetic analogues c-di-tzGMP, c-GtzGMP and c-GthGMP inducing earlier and stronger maximum IFN-β response compared to the native c-di-GMP (FIG. 3; see also Figures. S3a,b in Yi et al, ChemBioChem, Volume 21 (2020)). This pattern might result from negative feedback mechanisms of the CDNs-activated STING pathway and type-I IFN signaling.[17] The inventor speculate that rapid and potent IFN induction might concomitantly activate early negative feedback responses, which ultimately result in down tuning IFN-β production.

Among the synthetic CDNs tested in RAW 264.7 cells, the two analogues containing thG, the least isomorphic G surrogate that lacks the basic N7 in the native purine scaffold, displayed dramatically different potency in activating the STING pathway, with c-di-thGMP appearing essentially inactive, while c-GthGMP exerting the strongest effect on IFN-β induction of all analogues tested. This stark difference was also observed in the THP-1 human cell line, although c-GthGMP showed comparable potency to c-di-GMP (FIG. 1). These findings could reflect differences in the assay themselves. RT-qPCR detects IFN-β mRNA levels and not necessarily the translated active protein levels, whereas the reporter assay detects secreted type I interferons, including both IFN α and β. Additionally, the difference between cell lines could be rationalized by the existence of multiple STING alleles in human cells compared to murine cells, which possess different sensitivity to CDNs. [7c,18]

The observed intensity and duration of the cellular signaling response reflect both the affinity of the ligand to STING, as well as its resistance to intracellular degradation processes (assuming negligible differences in transfection efficiencies). It is perhaps not surprising that c-di-thGMP does not serve as a potent STING agonist, as it is the least isomorphic CDN analogue, with two altered purine cores. However, retaining one native G residue, as in c-GthGMP, restores STING activation. This result is consistent with observations made for other asymmetric CDNs, 3',3'-cGAMP and 2',3'-cGAMP, that also induce more potent STING activation than c-di-GMP. [8a,12a,19] Either through enhanced binding affinity to STING or potentially increased resistance to hydrolytic degradation, c-GthGMP induces a faster and greater innate immune response relative to the native signal c-di-GMP in murine cells. It would be worthwhile to further investigate the binding affinity of these CDN analogues to different STING variants, to further build correlations with their biological activity. In this context, the intrinsic fluorescence of our modified CDNs could potentially provide an effective tool to facilitate such studies.

Modifying the phosphate and sugar moieties of CDNs has been explored as a strategy to alter the pharmacological potency of STING agonists. Most of the noncognate base-modified CDNs have not been tested in immune response assays.[14f] Here we illustrate that a systematic modification of the nucleobases, rather than the phosphate or sugar moieties, can generate STING agonists that are more potent than c-di-GMP. Particularly intriguing is the high potency of the mixed analogues c-GthGMP and c-GtzGMP, where only one of the native guanosine residues is replaced by an unnatural synthetic C-nucleoside. Recognizing the complexity and intricacies of such cellular pathways, these observations put forth new approaches for the implementation of novel CDN analogues with altered recognition features, where the potency and duration of the triggered cellular immune response can be tuned.

Materials and Methods

Cell cultures. The RAW 264.7 cells were cultured in DMEM (Gibco) supplied with 2 mM L-glutamine, 10% fetal bovine serum (FBS) (Sigma), with or without 1% penicillin and streptomycin. The THP-1 cells were cultured in RPMI (Gibco) supplied with 2 mM L-glutamine, 10% heat-inactivated FBS, 10 mM HEPES (Gibco), 1 mM sodium pyruvate (Gibco), 0.25% glucose (Sigma), 0.05 mM 2-mercaptoethanol (Gibco). The HEK-Blue human type-I IFN reporter cells were cultured in DMEM (Gibco) supplied with 4.5 g/L glucose, 2 mM L-glutamine, 10% heat-inactivated FBS, 50 U/mL penicillin, 50 μg/mL streptomycin, 100 μg/mL Normocin. The cells were maintained at 37° C. under an atmosphere of 5% CO2/95% air.

Immunoblotting. RAW 264.7 cells were plated on 24-well plates (5×105 cells per well) and incubate at 37° C. for 48 h. Cells were then transfected with 1-10 μM of CDN in a permeabilization buffer containing 10 μg/mL digitonin, 50 mM HEPES, pH 7, 100 mM KCl, 3 mM MgCl2, 85 mM sucrose, 1 mM ATP, 0.1 mM DTT, 0.2% BSA for 30 mins at 37° C., then incubated with regular growth medium for 2 h. Cells were lysed with NP-40 lysis buffer containing protease inhibitor cocktail (Roche), PhosSTOP (Roche) and PMSF, and total protein was collected and quantified by BCA assay. Protein extracts were resolved by SDS-PAGE with 7.5% gel and transferred to PVDF membrane. Proteins were detected with the following primary antibodies: rabbit anti-pIRF3 monoclonal antibody (Cell Signaling Technology), mouse anti-β actin monoclonal antibody (Sigma-Aldrich).

RT-qPCR. RAW 264.7 cells were plated on 48-well plates (2.5×105 cells per well) and transfected with CDN using the same method as above after 48 h of incubation at 37° C. Cells were then incubate with regular growth medium for designated time, and total RNA was isolated with TRIzol® reagent and purified with RNeasy mini kit (Qiagen) following the manufacturer's protocol. Following elution, RNA yields were evaluated using a Nanodrop spectrophotometer (Nanodrop technologies). RNA samples were converted to cDNA with SuperScript III First-Strand Synthesis kit (Invitrogen) with random hexamers following the manufacturer's protocol. Quantitative PCR (SYBR Green) analysis was performed in duplicates on an Applied Biosystems 7300 Real-time PCR system (Invitrogen). Transcription level of IFN-β gene of each sample was normalized to housekeeping gene TBP and then to untreated samples (UT) using the delta-delta CT method.

Detecting type-I IFN production with reporter cells. THP-1 cells were seeded at a density of 100,000 cells/well in a 96-well cell culture plate and differentiated with 25 nM of phorbol myristate acetate (PMA) for approximately 20 h prior to treatment with CDNs. Cells were transfected with 5 μM of CDNs in a permeabilization buffer containing 5 μg/mL of digitonin, 50 mM HEPES, pH 7, 100 mM KCl, 3 mM MgCl2, 85 mM sucrose, 1 mM ATP, 0.1 mM DTT, 0.2% BSA and then washed and incubated in RPMI medium with 2% FBS at 37° C. for 4 h. 50 μL of the cell culture supernatant per well was transferred to 150 μL of HEK-Blue human type-I IFN reporter cells seeded at 50,000 cells/well in a 96-well cell culture plate and incubated at 37° C. overnight. The reporter cells were spun down the next day, and 50 μL of cell culture supernatant per well was transferred to a 96-well plate and added with 150 μL of QUANTI-Blue™ SEAP detection medium (InvivoGen) prepared according to the manufacturer's instructions. The samples were then incubated at 37° C. for 80 min before absorption was measured at 640 nm with an EnSpire plate reader (PerkinElmer). The absorption signal of each sample was normalized to untreated samples (UT).

Example 3

Figure 4:
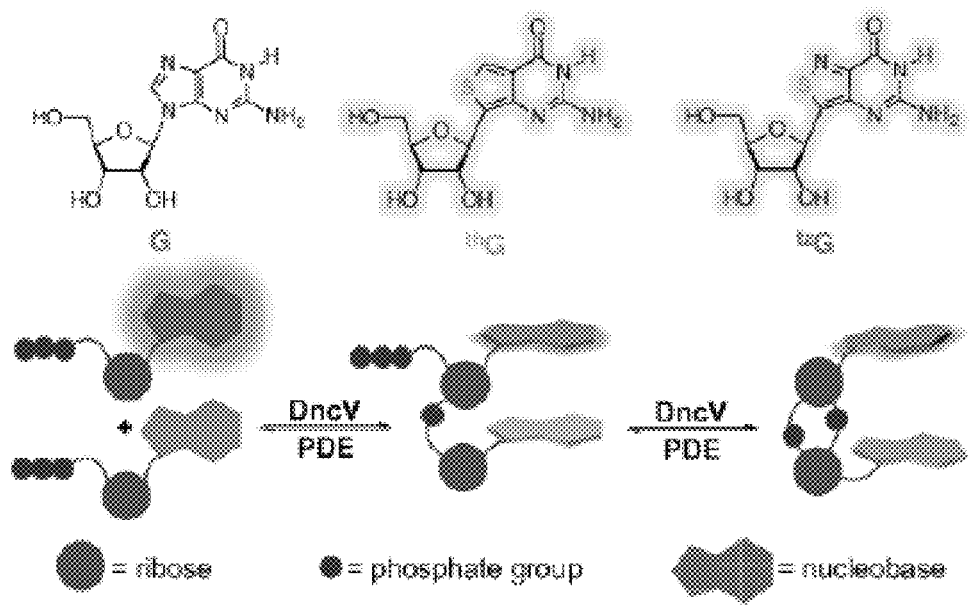
FIG. 4 shows the chemical structure of guanosine (G) and its emissive surrogates $^{th}$G and $^{tz}$G, and provides a hypothetical model predicting fluorescence changes upon CDN formation and hydrolysis.

Recent efforts by the inventors yielded two families of isomorphic emissive ribonucleosides, the thiopheno- and iso-thiazolo-based RNA alphabets ($^{th}N$ and $^{tz}N$, respectively). [11] The two families display distinctive photophysical properties and have been used to investigate catalytic RNAs, nucleoside metabolizing enzymes and diverse nucleotide-based cofactors.[12] The inventors surmised that the isomorphic fluorescent purine analogues' visible emission and sensitivity to environmental changes could be exploited to study the enzymes involved in CDNs biosynthesis and degradation, as schematically shown in FIG. 4.

While polymorphic, prone to aggregation and highly dependent on conditions, c-di-GMP displays stacking of the two nucleobases in solution.[13] This indicates distinct photophysics for any CDN compared to that displayed by its precursors (NTPs) or degraded products (pN or pNpN). The inventors further hypothesized that when thGTP or tzGTP would cyclize to the corresponding CDNs, the fluorescence would likely diminish and, conversely, phosphodiester hydrolysis of emissive CDNs would lead to fluorescence enhancement (FIG. 4). Such signal change can thus be used to monitor the process in real-time, determine reaction kinetics and, in principle, be used to facilitate inhibitor discovery. Herein we report the fluorescence-based monitoring of CDN synthesis and hydrolysis using thG and tzG, two isomorphic guanosine surrogates (FIG. 4). The resulting structure-activity relationship provides insight into the substrate recognition and catalytic mechanisms of the cyclase and CDN-specific PDEs studied.

Enzymatic Synthesis of c-Di-GMP Analogues with DncV

CDN analogues have greatly facilitated mechanistic, biochemical and structural studies, particularly in the context of CDN-binding riboswitches and protein receptors. [7b,9,14] The biggest hindrance to such studies has frequently been the preparation of analogues, as they have been predominately stepwise synthesized using phosphoramidite chemistry. [7b,15] The inventors employed DncV, a cyclic dinucleotide synthetase from *Vibrio cholerae*, to enzymatically produce a series of c-di-GMP analogues, as shown in Example 1. While this enzyme primarily synthesizes 3',3'-c-GAMP in vivo, when provided with only GTP or ATP in vitro it is also capable of making c-di-GMP and c-di-AMP. [16] Since DncV can accept both guanosine and adenosine, we postulated it would tolerate the thiopheno and isothiazolo G surrogates, members of our previously synthesized emissive RNA alphabets (FIG. 4).[11]

Figure 5:
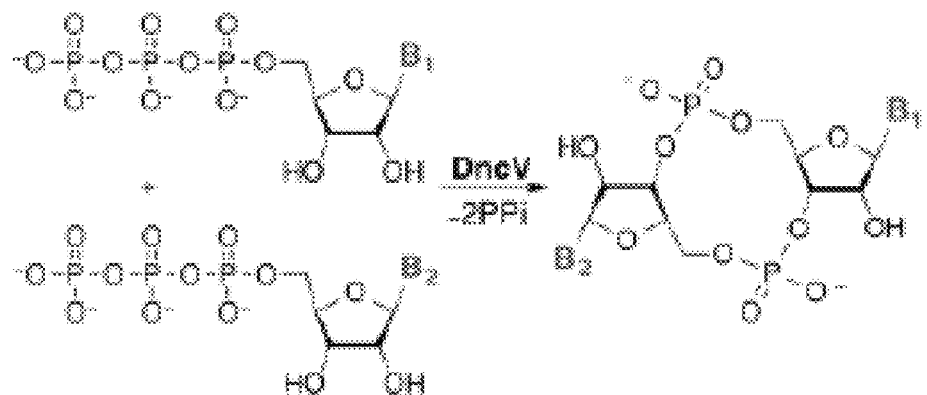
FIG. 5 shows the structures of the enzymatically synthesized ci-di-GMP analogues, and that DncV is able to convert two NTPs into the corresponding homo- and heterocyclic dinucleotides. B$_1$ (equivalent to R$^1$ herein) and B$_2$ (equivalent to R$^2$ herein) are nucleobases.

To benchmark the enzymatic synthesis of c-di-GMP and the corresponding emissive analogues, DncV was incubated with GTP, $^{th}$GTP and $^{tz}$GTP (FIG. 5). The reactions were analyzed by HPLC and mass spectrometry (FIG. 6, Supporting Information for Li et al, Chem Eur. J. 26:6076-6084 (Apr. 28, 2020)). After 40 minutes of incubation with 500 µM GTP, $^{tz}$GTP or $^{th}$GTP at 37° C., c-di-GMP, c-di-$^{tz}$GMP and c-di-$^{th}$GMP were obtained in 94%, 81% and 11% yields, respectively. DncV also produced the mixed c-G$^{tz}$GMP when incubated with 500 µM each of GTP and $^{tz}$GTP (Supporting Information for Li et al, Chem Eur. J. 26:6076-6084 (Apr. 28, 2020)). When incubated with a mixture of 500 µM of GTP and $^{th}$GTP, DncV also produces all three plausible products c-di-GMP, c-G$^{th}$GMP and c-di-$^{th}$GMP (Supporting Information for Li et al, Chem Eur. J. 26:6076-6084 (Apr. 28, 2020)). Based on HPLC analyses shown in FIG. 6, the overall yields of c-di-GMP (40 mins), c-di-$^{tz}$GMP (80 mins), and c-di-$^{th}$GMP (300 mins) were 94%, 85% and 62%, respectively. These results have indeed confirmed the tolerance level of DncV to $^{th}$GTP and $^{tz}$GTP, our emissive NTPs. Both symmetric and mixed CDN analogues were successfully synthesized in this fashion.

DncV generates CDNs through a series of sequential reactions, which are thought to involve a release-and-rebound process of the intermediate. [7b,17] After the first 3',5'-phosphodiester bond formation, the linear dinucleotide pppNpN is released and oppositely rebound to the enzyme, after which the second 3',5'-phosphodiester linkage is made. [7b,16b,18] To ultimately apply and interpret real-time fluorescence measurements, a better understanding of the enzymatic conversion of GTP and its analogues into the corresponding CDNs is therefore required. The reaction time course was consequently analyzed, paying particular attention to the accumulation and consumption of intermediates. DncV was incubated with GTP, tzGTP and thGTP, and the reactions containing each of the corresponding substrates were quenched with calf intestinal alkaline phosphatase (CIAP) at designated time points. [19] The relative concentrations of the starting material (S), uncyclized intermediate (I) and product (P) were then monitored by HPLC. The integrated area under the peak for each species was corrected using the corresponding extinction coefficient and normalized to its relative concentration, which were then plotted against time. Taking into account the unique release-and-rebound process of the uncyclized dinucleotide intermediate, [16b,20] the kinetics of the DncV-mediated CDN syntheses was therefore analyzed according to the model in Scheme 1a and the differential Equations (1)-(4), in which S represents the starting NTP, $I_1$ and $I_2$ respectively represent intermediates pppNpN and degraded intermediate pNpN (I=$I_1$+$I_2$), and P represents the product CDN. Papp (apparent product) stands for the sum of all the dinucleotide species, including linear ones and cyclized products.

Scheme 1a

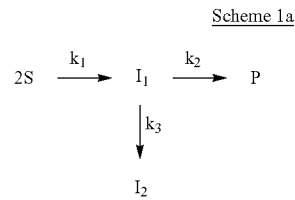

Differential Equations (1)-(4)

$$d[S]/dt=-2k_1[S]^2 \qquad (1)$$

$$d[I_1]/dt=k_1[S]^2-k_2[I_3]-k_3[I_3] \qquad (2)$$

$$d[P]/dt=k_2[I_3] \qquad (3)$$

$$d[I_2]/dt=k_3[I_1] \qquad (4)$$

A small amount of uncyclized intermediate was observed during the synthesis of c-di-GMP (FIGS. 6A-6C), and the calculated $k_1$, $k_2$ and $k_3$ values were found to be $(7.1\pm2.3)\times 10^{-6}$ µM$^{-1}$s$^{-1}$, $(7.4\pm2.1)\times10^{-2}$ and $(6.4\pm0.3)\times10^{-4}$s$^{-1}$, respectively (Table 1, where the data is presented as mean±SD).

TABLE 1

| Reaction Rate Constants of DncV-mediated CDN syntheses | | | |
|---|---|---|---|
| | $k_1$ (µM$^{-1}$s$^{-1}$) | $k_2$ (s$^{-1}$) | $k_3$ (s$^{-1}$) |
| c-di-GMP | (7.1 ± 2.3) × 10$^{-6}$ | (7.4 ± 2.1) × 10$^{-2}$ | (6.4 ± 0.3) × 10$^{-4}$ |
| c-di-$^{tz}$GMP | (1.26 ± 0.07) × 10$^{-6}$ | (3.4 ± 0.2) × 10$^{-3}$ | (1.3 ± 0.1) × 10$^{-4}$ |
| c-di-$^{th}$GMP | (3.08 ± 0.03) × 10$^{-7}$ | (2.32 ± 0.05) × 10$^{-4}$ | (2.91 ± 0.01) × 10$^{-5}$ |

Figure 6A:
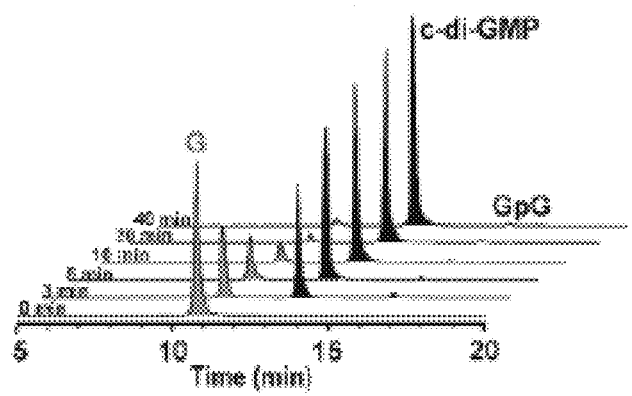
FIGS. 6A-6I show DncV-mediated enzymatic synthesis of c-di-GMP and its analogues c-di-$^{tz}$GMP and c-di-$^{th}$GMP.
Figure 6B:
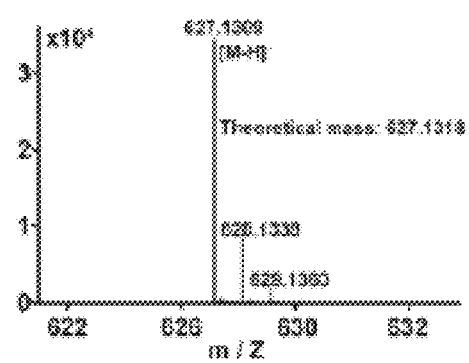
Figure 6C:
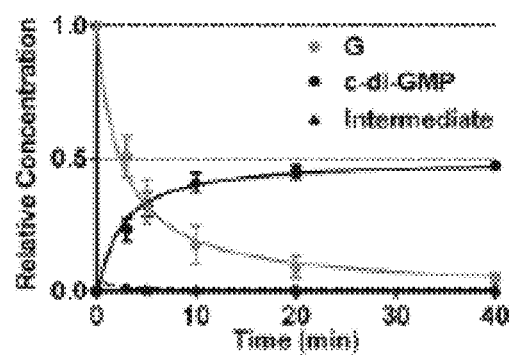
Figure 6D:
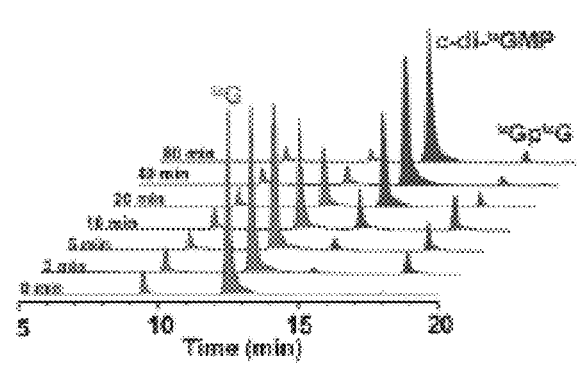
Figure 6E:
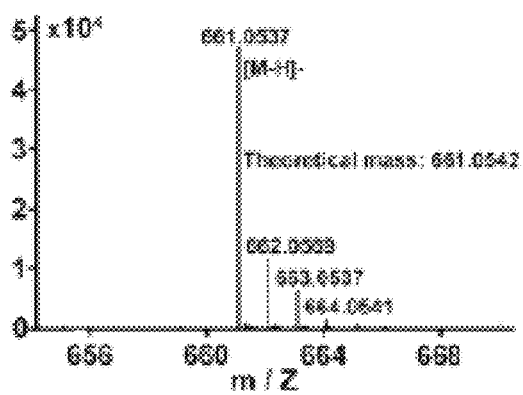
Figure 6F:
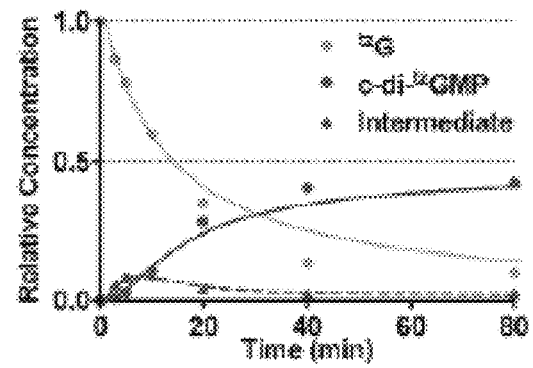
Figure 6G:
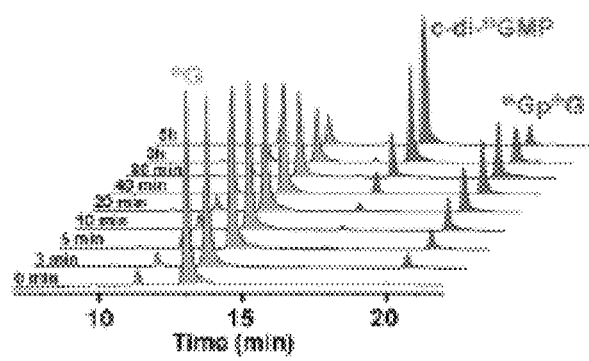
Figure 6H:
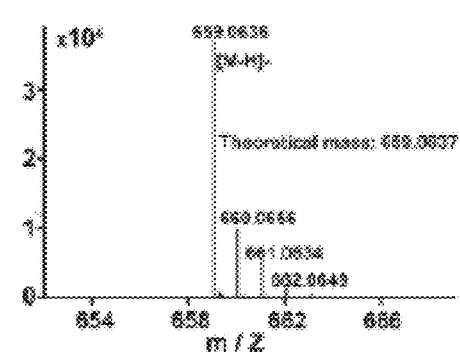
Figure 6I:
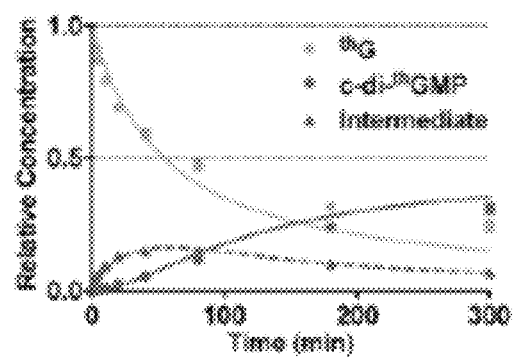

When incubated with tzGTP, a larger amount of the intermediate was accumulated in the first 10 minutes resulting in an S-shaped product formation curve (FIGS. 6D-6F). [21] The calculated k1, k2 and k3 values were $(1.26\pm0.07)\times 10^{-6}$ µM$^{-1}$s$^{-1}$, $(3.4\pm0.2)\times10^{-3}$ and $(1.3\pm0.1)\times10^{-4}$s$^{-1}$, respectively. DncV was also found to convert thGTP into the corresponding c-di-thGMP with k1, k2 and k3 values of $(3.08\pm0.03)\times10^{-7}$ µM$^-$s$^{-1}$, $(2.32\pm0.05)\times10^{-3}$ and $(2.91\pm0.01)\times10^{-5}$s$^{-1}$, respectively (FIGS. 6G-6I). After 5 h of incubation, 62% of thGTP was converted to c-di-thGMP. Obvious accumulation of the reaction intermediate is seen for the first 80 minutes (FIGS. 6G, 6I). The relatively fast degradation of the intermediate compared to product formation (k2/k3 was calculated to be 8.0 for c-di-thGMP synthesis, compared to 26 for c-di-tzGMP and 116 for c-di-GMP) resulted in relatively high concentration (13% after 300 min) of persistent uncyclized intermediates (FIG. 6I).

The guanosine surrogates used here illuminate the key functional elements in the purine scaffold that affect the formation and consumption of the reaction intermediate. The kinetic constants listed in Table 1 illustrate that the formation of the first phosphodiester linkage is the rate-limiting step for the syntheses of c-di-GMP, c-di-tzGMP and c-di-thGMP. [22] Furthermore, a certain fraction of the uncyclized intermediate is not entirely consumed in all three reactions (FIGS. 6C, 6F, 6I). We speculate that the hydrolysis of the open intermediate pppNpN ($I_1$ in Scheme 1a) to the unreactive pNpN ($I_2$ in Scheme 1a) could take place. [23] Additionally, the consumption of $^{th}$GTP in c-di-$^{th}$GMP synthesis was observed to be slower than calculated. We speculate that this might be caused by a non-productive DncV-mediated hydrolysis of thGTP to thG monophosphate ($p^{th}G$), circumventing the formation of the inter-nucleotide phosphodiester bond. Our findings support the hypothesis that the absence of the purine's N-7 can alter the reaction kinetics, although previous structural studies with DncV have not revealed a direct contact between N-7 of GTP and any protein residues. [16b,18,20]

Photophysical Properties of Emissive c-di-GMP Analogues

Figure 7A:
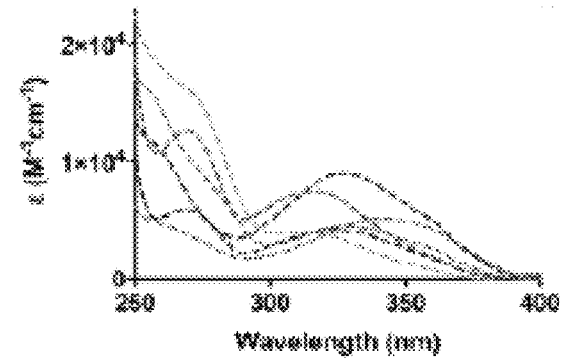
FIGS. 7A-7B are absorption spectra (FIG. 7A) and emission spectra (FIG. 7B)) of $^{th}$G (black), $^{tz}$G (grey), c-di-$^{th}$GMP (red), c-di-$^{tz}$GMP (indigo), c-G$^{th}$GMP (orange) c-G$^{tz}$GMP (light blue) dissolved in water. The emission spectra were normalized to optical density of 0.1 at the excitation wavelengths (320 and 330 nm for species containing $^{th}$G and $^{tz}$G, respectively).
Figure 7B:
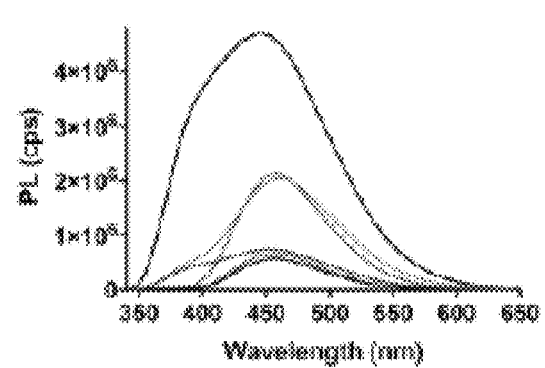
Figure 8A:
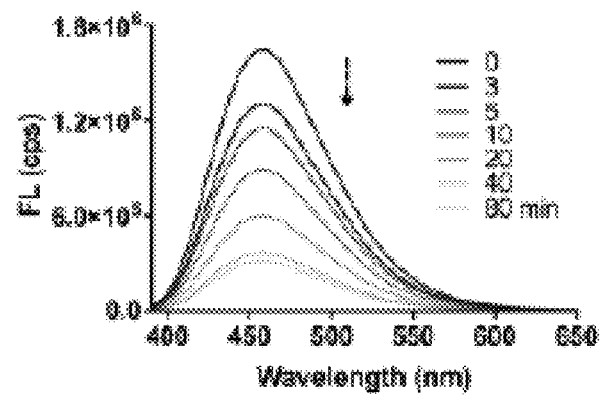
FIGS. 8A-8D are DncV-mediated cyclization monitored by emission spectra for (FIG. 8A) c-di-$^{tz}$GMP, (FIG. 8B) c-G$^{tz}$GMP, (FIG. 8C) c-di-$^{th}$GMP and (FIG. 8D) c-G$^{th}$GMP. Excitation wavelength was 380 nm for all emission spectra.
Figure 8B:
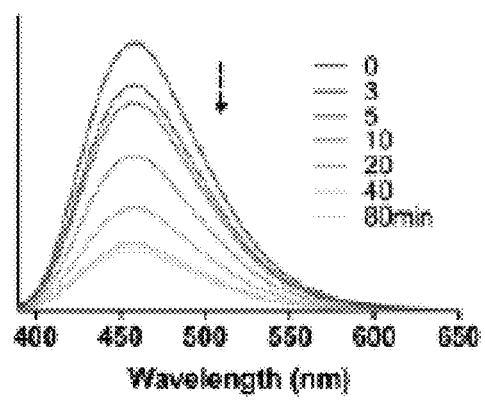
Figure 8C:
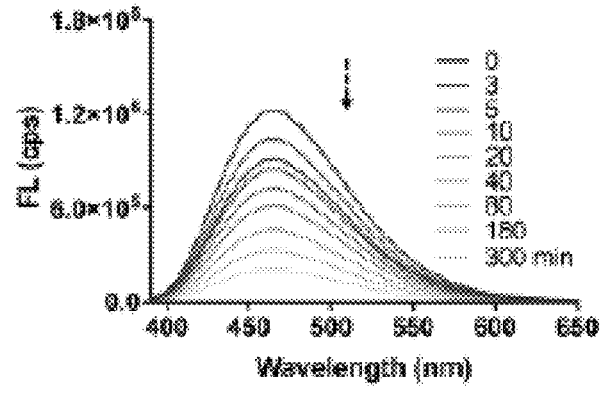
Figure 8D:
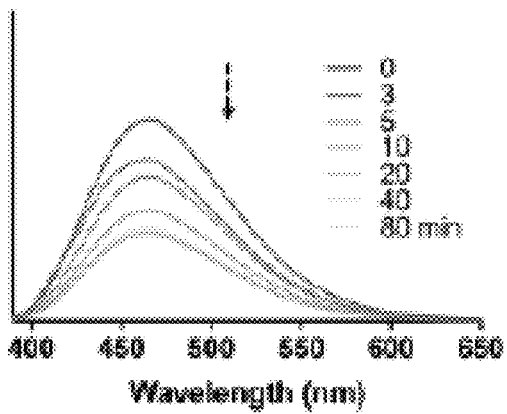

Steady-state absorption and emission measurements show hypsochromic shifts in the absorption maxima of thG and tzG upon incorporation into the corresponding cyclic dinucleotides (FIG. 7; Table 2, where values for $^{th}G$ and $^{tz}G$ were obtained from previous publications [11]).

TABLE 2

Photophysical Properties of Emissive Nucleosides and CDN analogues

|  | $\lambda^{max}_{abs}$ (nm) | $\varepsilon$ (M$^{-1}$cm$^{-1}$) | $\lambda^{max}_{em}$ (nm) | $\phi$ | $\phi\varepsilon$ |
|---|---|---|---|---|---|
| thG | 321 | 4.15 × 10$^3$ | 453 | 4.6 × 10$^{-1}$ | 1909 |
| tzG | 333 | 4.87 × 10$^3$ | 459 | 2.5 × 10$^{-1}$ | 1203 |
| c-di-thGMP | 317 | 7.47 × 10$^3$ | 457 | 7.7 × 10$^{-2}$ | 575 |
| c-di-tzGMP | 331 | 8.77 × 10$^3$ | 456 | 3.9 × 10$^{-2}$ | 342 |
| c-GthGMP | 317 | 3.54 × 10$^3$ | 458 | 1.8 × 10$^{-1}$ | 636 |
| c-GtzGMP | 331 | 4.38 × 10$^3$ | 456 | 4.8 × 10$^{-2}$ | 210 |

While relatively small (<10 nm), this trend is suggestive of multichromophoric arrangements reminiscent of H-aggregates. [24] The emission energy of the $^{th}G$- and $^{tz}G$-containing CDNs remains relatively close to that of the parent nucleosides and, intriguingly, the $^{th}G$-containing derivatives still display the high energy shoulder associated with its tautomeric forms. [25] Comparing the emission quantum yields (F) of the fluorescent CDNs to those of the monomeric nucleosides show significant quenching of the former, as predicted (Table 2). Interestingly, $^{th}G$ exhibits a significantly enhanced self-quenching effect relative to guanosine; the emission quantum yield values for c-di-$^{th}$GMP and c-G$^{th}$GMP were about 17% and 39% of $\phi^{th}_G$, respectively. The self-quenching effect of $^{tz}G$ resulted in the low quantum yield for c-d-$^{tz}$GMP (16% of $\phi^{tz}_G$), which is comparable to that seen for c-G$^{tz}$GMP (19% of $\phi^{tz}_G$). These results match the model illustrated in FIG. 4, where decreased emission intensity was expected upon the conversion of the emissive NTPs into CDNs. Further analysis below provides additional insight into this model and its potential applications.

Monitoring DncV-Mediated Synthesis of c-Di-GMP Analogues with Fluorescence

The significant difference in emission seen for nucleotides compared to the corresponding CDNs, can be exploited for monitoring the enzymatic transformations. The bacterial enzyme DncV was thus incubated with either GTP, $^{th}$GTP, $^{tz}$GTP or mixtures thereof under the same conditions as the HPLC-monitored reactions. Aliquots were treated with calf intestinal alkaline phosphatase (CIAP) at designated times, and emission spectra were taken after appropriate dilution. Rewardingly, significantly diminished fluorescence intensities were observed for the syntheses of all four homodimeric and mixed fluorescent c-di-GMP analogs, as hypothesized (FIG. 8).

Unlike integrated chromatographic analyses, which can separately account for all individual species present, the observed fluorescence signal reflects the sum of all emissive species. To facilitate quantitative analyses of fluorescence data, a conversion factor (a) was introduced to the simulation of the fluorescence-monitored reaction kinetics. This factor bridges the integrated fluorescent spectrum and the concentration of a given chromophore at a given set of conditions and can be calculated from the integrated emission spectrum ($FL_{int}$) of a given chromophore with known concentration ([C]) using Equation (5). Since photophysical properties can be affected by reaction conditions, such as pH, ionic strength and temperature, a values are measured under identical conditions as the enzymatic reactions (Supporting Information for Li et al, Chem Eur. J. 26:6076-6084 (Apr. 28, 2020)). To compare the fluorescence- and HPLC-monitored reaction kinetics, Equation (6) was used to correlate the recorded fluorescence spectrum with the concentrations of different species in the reaction mixture. As a first attempt, the k values extracted from the HPLC analysis were used to fit the fluorescence data (referred to as FL Model 1).

$$FL_{int} = a[C] \quad (5)$$

$$FL_{int} = a_1[S] + a_2[I_1] + a_3[P] + a_4[I_2] \quad (6)$$

Figure 9A:
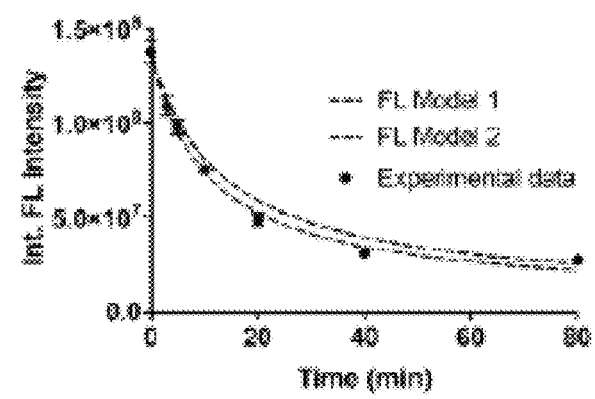
FIGS. 9A-9B are kinetics analysis of DncV-mediated synthesis of (FIG. 9A) c-di-$^{tz}$GMP ($R^2$=0.9759, 0.995 for FL model 1 and FL model 2, respectively) and (FIG. 9B) c-di-$^{th}$GMP ($R^2$=0.8325, 0.9205 for FL model 1 and FL model 2, respectively).
Figure 9B:
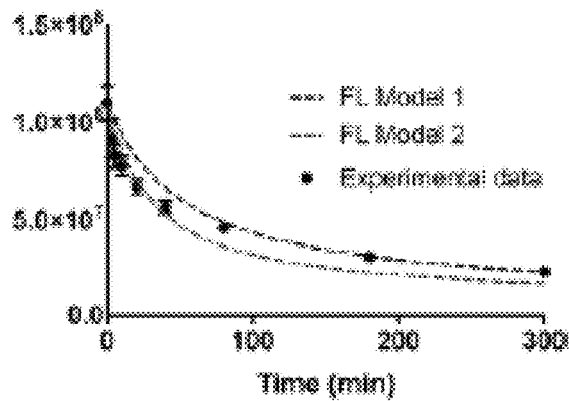

Whereas $a_1$ and $a_3$ could be successfully measured for the starting materials and final products, $a_2$ and $a_4$ are difficult to obtain, since the intermediates are produced in small quantities. We therefore first assume that $a_2$ is approximately equal to $a_3$ is approximately equal to $a_4$ in Eq. 6. The calculated curve fitted well to the experimental data for c-di-$^{tz}$GMP synthesis with $R^2 = 0.976$, indicating excellent agreement between the reactions monitored by HPLC and fluorescence (FIG. 9A). For c-di-$^{th}$GMP synthesis, the observed fluorescence signal decreased faster than modeled for the first 40 minutes (FIG. 9B), which resulted in a poorer fit ($R^2 = 0.833$). In addition to the previously discussed reasons, potentially leading to poorly simulated curves for this HPLC analyzed reaction (FIG. 6I), the significant accumulation of intermediates ($p^{th}Gp^{th}G$ or $ppp^{th}Gp^{th}G$) during the first 80 minutes, hampers the simulation of its fluorescence response. Possible differences between the photophysical properties of the intermediates and the product are thus more influential on the analysis of c-di-$^{th}$GMP synthesis as our assumption of $a_2$ is approximately equal to $a_3$ is approximately equal to $a_4$ in Equation 6 is challenged.

In addition to using chromatographically determined k values (Scheme 1a), we also simplified the analysis of the homodimeric CDNs synthesis to a pseudo-second order reaction (Scheme 1b).

Scheme 1b

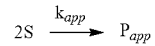

This approach relies on the observation that the intermediates are present in relatively low concentrations (and hence contribute less to the overall fluorescence signal). The apparent kinetics rate constant ($k_{app}$) was extracted with Equations (7)-(9) (referred to as FL Model 2).

$$d[S]/dt = -2k_{app}[S]^2 \quad (7)$$

$$d[P_{app}]/dt = k_{app}[S]^2 \quad (8)$$

$$FL_{int} = a_1[S] + a_3[P_{app}] \quad (9)$$

Based on our hypothesis, $k_{app}$ in Scheme 1b should be comparable to $k_1$ in Scheme 1a, as the major contributor to the change in fluorescence signal is the formation of the first intermediate ($I_1$). Rewardingly, using FL Model 2, the simulated curve fits well the experimental data for c-di-$^{tz}$GMP with $R^2 = 0.995$, and derived $k_{app} = 1.57 \pm 0.15$ $M^{-1}s^{-1}$, which is close to the $k_1$ derived from HPLC analysis ($1.26 \pm 0.07$ $M1^{-1}s^{-1}$) (FIG. 9A; Supporting Information for Li et al, Chem Eur. J. 26:6076-6084 (Apr. 28, 2020)). Similar to FL model 1, the simulation curve did not fit as well for the synthesis of c-di-$^{th}$GMP ($R^2 = 0.921$, FIG. 9B). The $k_{app}$ value derived from the pseudo-second order simulation was slightly larger than the k1 values derived from HPLC analysis ($0.53 \pm 0.05$ and $0.31 \pm 0.03$ $M^{-1}s^{-1}$, respectively), but overall the two k values were still comparable (Supporting Information for Li et al, Chem Eur. J. 26:6076-6084 (Apr. 28, 2020)). The accumulation of intermediates during c-di-$^{th}$GMP synthesis makes the simplification to a pseudo-second order reaction challenging. Adjusting the apparent rate constant yields only minor improvement for the simulation. Nevertheless, these observations reflect our previous observations, highlighting the higher isofunctionality of the isothiazolo family of purine surrogates compared to the thiopheno family. [12d,26]

RocR-Mediated CDN Hydrolysis Monitored by HPLC

Beside the cyclases that synthesize c-di-GMP, its hydrolysis to linear pGpG or GMP by PDEs is key to controlling the global and local concentration of such messengers in bacteria and hence to regulating downstream processes. [1a,27] rocR is a PDE that contains an EAL domain and specifically recognizes and cleaves c-di-GMP into the linear dinucleotide pGpG. [28] It is one of P. aeruginosa's most active and well-studied PDEs. [28a,29] To shed light on the substrate-enzyme interactions and its suitability for fluorescence monitoring, enzymatically synthesized c-di-GMP, c-di-$^{tz}$GMP, c-di-$^{th}$GMP, c-G$^{th}$GMP and c-G$^{tz}$GMP were incubated with rocR, and the relative concentrations of the starting material (CDN) and product (pNpN) at designated time points were monitored by HPLC (Supporting Information for Li et al, Chem Eur. J. 26:6076-6084 (Apr. 28, 2020)). Notably, the assigned identity of the products was confirmed by LC-ESI-TOFMS (Supporting Information for Li et al, Chem Eur. J. 26:6076-6084 (Apr. 28, 2020)).

RocR is reported to follow Michaelis-Menten kinetics. [27c,28a] Scheme 2a was therefore used to analyze the reaction kinetics, where $k_1$ and $k_{-1}$ describe the enzyme/substrate association and dissociation, respectively, while $k_2$ reflects the cleavage reaction. Equations (10)-(13) were thus used to extract the rate constants. When "asymmetrical" mixed c-di-GMP analogues are treated with rocR, the enzyme may, in principle, recognize and cleave either phosphodiester bonds, producing $pN_1pN_2$ and $pN_2pN_1$. Assuming the two products result from different binding orientation of the heterodimeric CDNs, Scheme 2b is therefore introduced to model the cleavage reactions, where $k_1$, $k_{-1}$ and $k_2$ reflect the association/dissociation and cleavage of the heterodimeric CDN in one orientation, respectively, and $k_3$, $k_{-3}$ and $k_4$ reflect the other. Equations (14)-(19) were used to extract the rate constants.

Scheme 2a

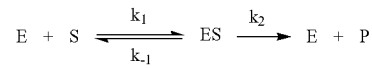

Scheme 2b

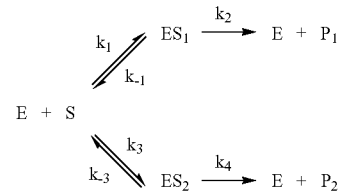

Figure 10A:
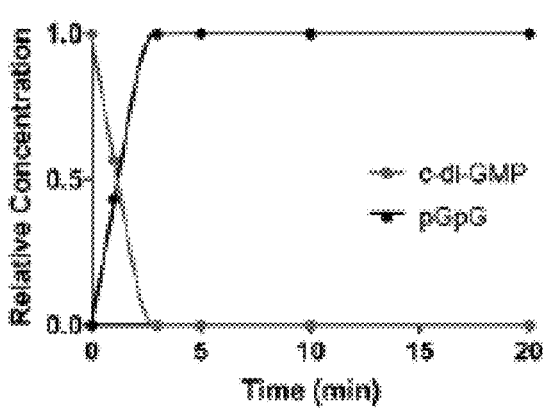
FIGS. 10A-10F are kinetics analyses of rocR-mediated cleavage of c-di-GMP analogues. The enzyme (100 nM) was incubated with 10 mM of (FIG. 10A) c-di-GMP, (FIG. 10B) c-di-$^{tz}$GMP, (FIG. 10C) c-di-$^{th}$GMP, (FIG. 10D) c-G$^{th}$GMP and (FIG. 10E) c-G$^{tz}$GMP and the reactions were quenched using 100 mM CaCl$_2$ at designated time point and analyzed by HPLC. Assays were done in duplicates. Error bars indicate SD.
Figure 10B:
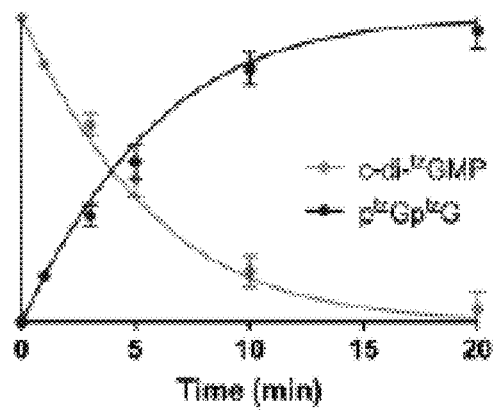
Figure 10C:
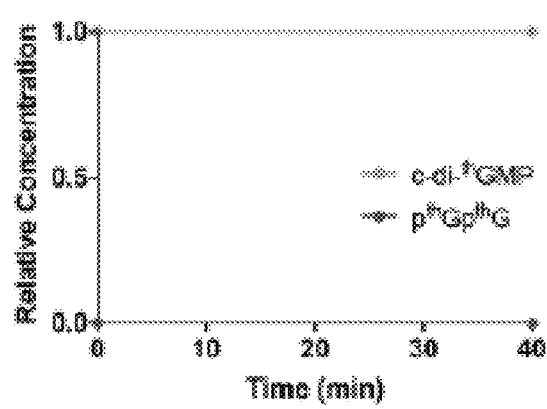
Figure 10D:
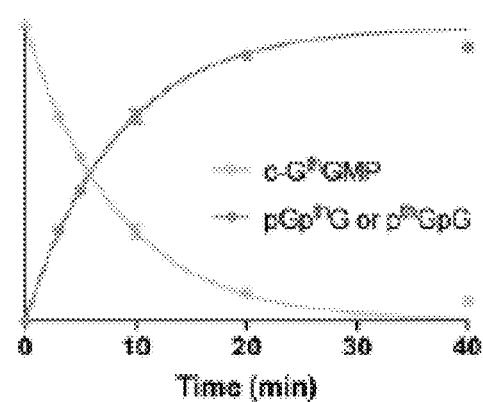
Figure 10E:
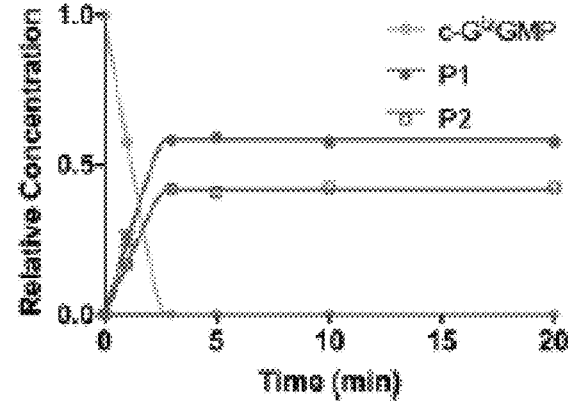
Figure 10F:
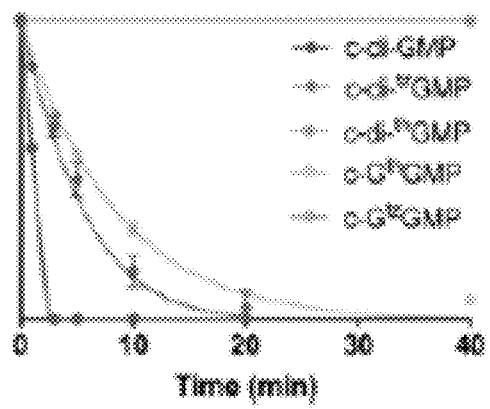
Figure 11A:
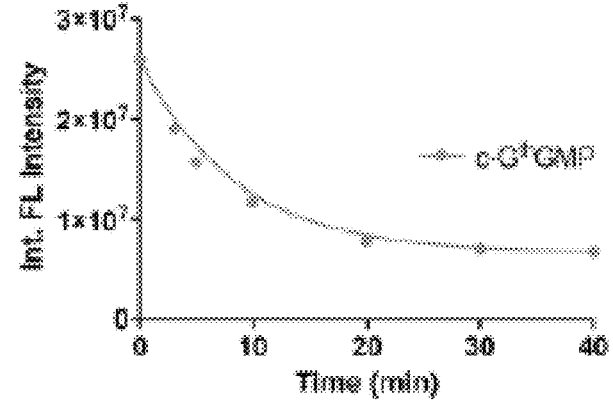
FIGS. 11A-11B show rocR-mediated CDN hydrolysis monitored with fluorescence.
Figure 11B:
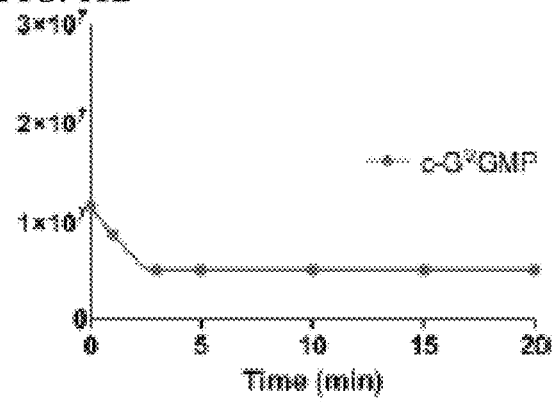

Equations (10)-(19)

$$d[S]/dt = -k_1[E][S] + k_{-1}[ES] \quad (10)$$

$$d[E]/dt = -k_1[E][S] + k_{-1}[ES] + k_2[ES] \quad (11)$$

$$d[P]/dt = k_2[ES] \quad (12)$$

$$d[ES]/dt = k_1[E][S] - k_{-1}[ES] - k_2[ES] \quad (13)$$

$$d[S]/dt = -k_1[E][S] + k_{-1}[ES_1] - k_3[E][S] + k_{-3}[ES_2] \quad (14)$$

$$d[P_1]/dt = k_2[ES_1] \quad (15)$$

$$d[P_2]/dt = k_4[ES_2] \quad (16)$$

$$d[E]/dt = -(k_1+k_3)[E][S] + (k_{-1}+k_2)[ES_1] + (k_{-3}k_4)[ES_2]] \quad (17)$$

$$d[ES_1]/dt = k_1[E][S] - k_{-1}[ES_1] - k_2[ES_1] \quad (18)$$

$$d[ES_2]/dt = k_3[E][S] - k_{-3}[ES_2] - k_4[ES_2] \quad (19)$$

c-di-GMP was completely cleaved by rocR to pGpG in nearly 3 minutes with $k_1 = 3.96 \pm 0.07$ $mM^{-1}$ $s^{-1}$ and $k_2 = 0.76 \pm 0.03$ $s^{-1}$ (FIG. 10A, Table 3). Enzymatic cleavage of c-di-$^{tz}$GMP was slower compared to c-di-GMP, but was completed within 20 min (FIG. 10B) with $k_1 = 0.043 \pm 0.02$ $\mu M^{-1}$ $s^{-1}$ and $k2 = 0.83 \pm 0.55$ $s^{-1}$ (Table 3). No cleaved c-di-$^{th}$GMP was observed after 40 min of incubation with rocR (FIG. 10C). The rocR-mediated cleavage of the mixed c-G$^{th}$GMP yielded a single product (FIG. 10C), either pGp$^{th}$G or p$^{th}$GpG, while two products in nearly the same amount were observed for c-G$^{tz}$GMP (Supporting Information for Li et al, Chem Eur. J. 26:6076-6084 (Apr. 28, 2020)), illustrating that both pGp$^{tz}$G and p$^{tz}$GpG were produced (FIG. 10E). Overall, a gradually reduced hydrolysis rate was observed as the structures progressively deviated from the parent CDN in the order: c-di-GMP, c-di-$^{tz}$GMP, c-G$^{tz}$GMP, c-G$^{th}$GMP and lastly c-di-$^{th}$GMP (FIG. 10F).

TABLE 3

Reaction Rate Constants for rocR-mediated CDNs cleavage

|  | $k_1$ (μM$^{-1}$s$^{-1}$) | $k_2$ (s$^{-1}$) | $k_3$ (s$^{-1}$) | $k_{-3}$ (μM$^{-1}$s$^{-1}$) | $k_{-3}$ (s$^{-1}$) | $k_4$ (s$^{-1}$) |
|---|---|---|---|---|---|---|
| c-di-GMP | 3.96 ± 0.07 | 1.15 ± 0.21 | 0.76 ± 0.03 | NA | NA | NA |
| c-di-$^{tz}$GMP | 0.043 ± 0.02 | 0.099 ± 0.07 | 0.83 ± 0.55 | NA | NA | NA |
| c-G$^{th}$GMP | 0.021 ± 0.001 | 0.033 ± 0.001 | 5 ± 0.57 | NA | NA | NA |
| c-G$^{tz}$GMP | 1.85 ± 0.07 | 0.096 ± 0.091 | 3.07 ± 0.25 | 1.8 ± 0.1 | 0.135 ± 0.007 | 0.34 ± 0.01 |

The observed relative rates of rocR-mediated hydrolyses of the CDN analogues indicate that the presence of a nitrogen at the purine's N-7 position on at least one nucleobase is necessary for efficient substrate recognition and cleavage. The enzyme did not produce observable amounts of cleaved c-di-$^{th}$GMP products after 40 min, while the majority of c-di-$^{tz}$GMP was found to be cleaved within 20 min, indicating that altering both N-7 positions is likely detrimental to rocR-mediated hydrolytic cleavage. With a single N-7-containing nucleobase such as in the mixed c-G$^{th}$GMP, only one phosphodiester bond is cleaved by rocR. In contrast, rocR was able to recognize the mixed c-G$^{tz}$GMP, where donor nitrogen atoms are present on both nucleobases, from both orientations, leading to cleavage of either phosphodiester bond and the release of pGp$^{tz}$G and p$^{tz}$GpG (FIG. 10E).

Crystal structure of rocR with a bound ligand has not yet been reported, thus systematically modified CDN analogues as studied here can illustrate the importance of the nucleobases in substrate recognition and cleavage. The structure of Ykul-bound c-di-GMP shows the amide group of the highly conserved Q16 (similar to Q161 of rocR) to be hydrogen bonded to the N-7 of the guanosine found 5' to the cleavage site. [27c,29-30] Indeed, mutation of rocR's Q161 caused a 5-fold decrease in kcat, and 2-fold increase in W, indicating that Q161 is involved in substrate recognition. [27c] We thus conjecture that the cleavage product of c-G$^{th}$GMP is pGp$^{th}$G and submit that there is little bias in rocR binding/cleaving of c-G$^{tz}$GMP in either orientation, as $k_1$ approximately equals $k_3$, and $k_{-1}$ approximately equals $k_{-3}$ (Table 3). The difference in the final percentage of the two products $P_1$ (58%) and $P_2$ (42%) (Scheme 2b) might be caused by different efficiencies for the phosphodiester bond cleavage, as k2 (3.07±0.25 s$^{-1}$) is much bigger than k4 (0.34±0.01 s$^{-1}$).

Monitoring CDN Hydrolysis with Fluorescence

To fluorescently monitor the rocR-mediated CDN hydrolysis, the enzymatic reactions with c-G$^{th}$GMP, c-G$^{tz}$GMP and c-di-$^{tz}$GMP were executed in cuvettes under the same conditions as the reactions monitored with HPLC, and emission spectra were taken at designated time points. As shown in FIG. 11 FIGS. 13A-13C, significant decrease of emission was observed during c-G$^{th}$GMP and c-G$^{tz}$GMP hydrolysis. The fitted curves were generated with the same rate constants derived from HPLC analysis. In addition to Equations (10)-(19), Equations (20) and (21) were used to correlate fluorescence signal with concentration for reactions described in Scheme 2a and 2b, respectively.[31] The fluorescence conversion factors (a) are shown in Table S4 in the Supporting Information for Li et al, Chem Eur. J. 26:6076-6084 (Apr. 28, 2020). The resulting R$^2$ values for c-G$^{th}$GMP and c-G$^{tz}$GMP hydrolysis monitored by fluorescence were 0.986 and 0.916, respectively. On the other hand, rocR-mediated c-di-$^{tz}$GMP hydrolysis did not lead to significant change in emission intensity (See FIG. S13c in the Supporting Information for Li et al, Chem Eur. J. 26:6076-6084 (Apr. 28, 2020)). It is possible that p$^{tz}$Gp$^{tz}$G and c-di-$^{tz}$GMP have similar photo-physical properties, suggesting that our assumption of $a_2$ is approximately equal to $a_3$ is approximately equal to $a_4$ in Eq. (6) when monitoring CDN synthesis with fluorescence stands well.

Equations(20)-(21)

$$FL_{int} = a_1[S] + a_2[P] \quad (20)$$

$$FL_{int} = a_1[S] + a_2([P_1] + [P_2]) \quad (21)$$

Figure 12A:
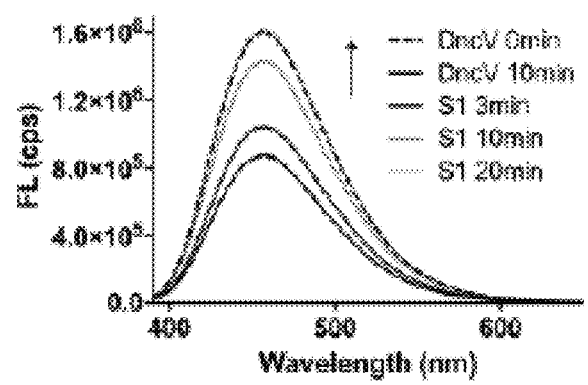
FIGS. 12A-12F provide DncV-mediated synthesis and S1 nuclease-mediated hydrolysis of CDNs monitored with emission spectra.
Figure 12B:
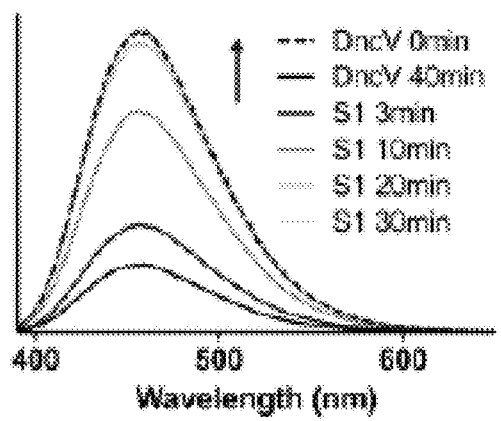
Figure 12C:
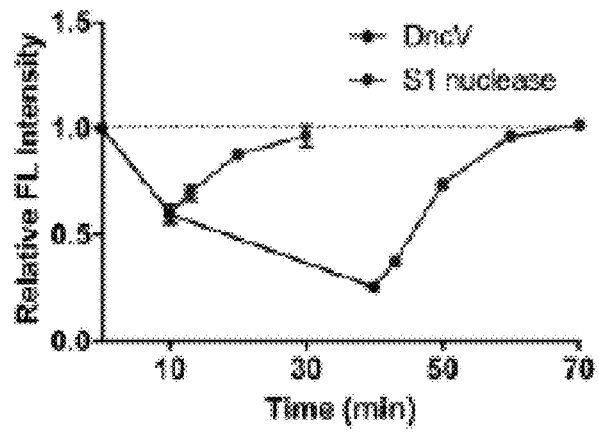
Figure 12D:
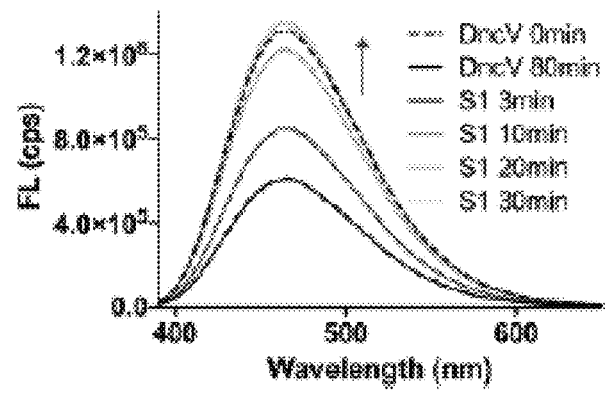
Figure 12E:
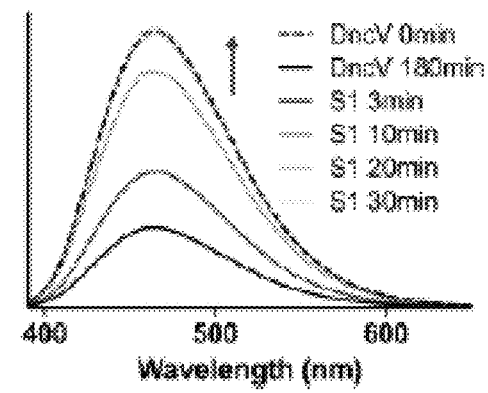
Figure 12F:
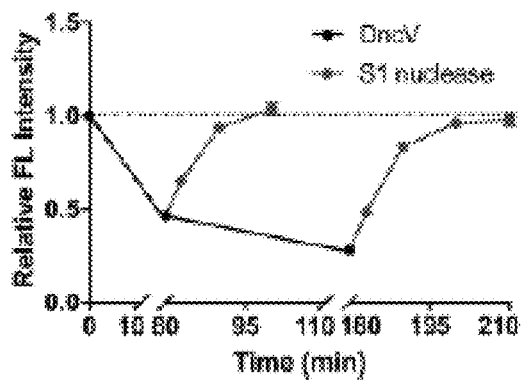
Figure 13A:
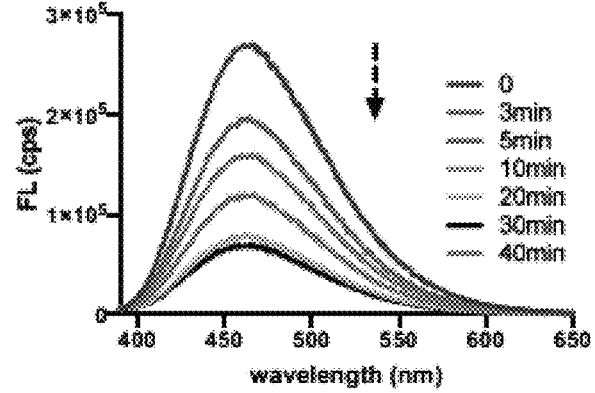
FIGS. 13A-13C provide rocR-mediated hydrolysis monitored by steady-state emission spectra for (FIG. 13A) c-Gth-GMP.
Figure 13B:
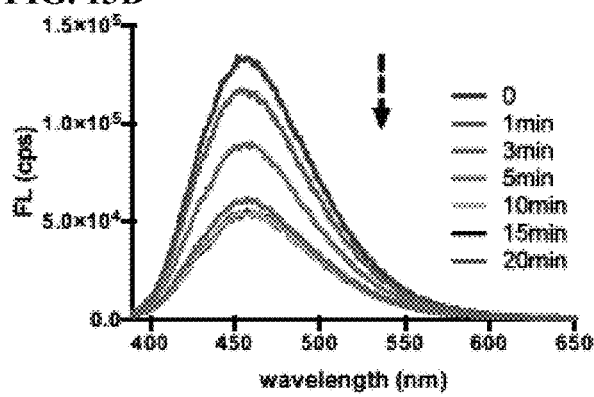
Figure 13C:
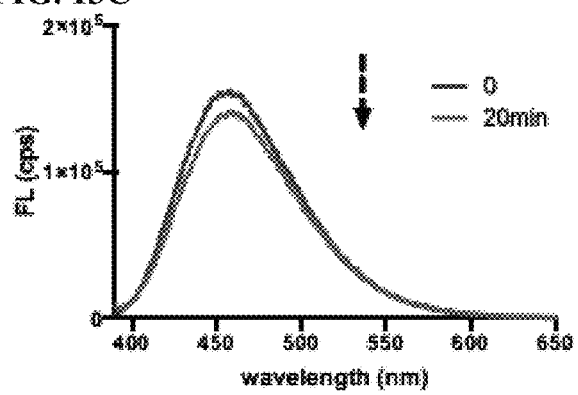

The relatively small differences in emission intensities of the CDNs and the corresponding rocR-cleaved linear products, reflects the complexity in foreseeing how changes in molecular structure impact the photophysical features. The quenching effect of fluorescent nucleosides in CDNs and their degradation products is indeed dependent on several factors associated with their building blocks, including their stacking distance and orientation, as well as their collisional dynamics and possibly aggregation. To further test the proposed model shown in FIG. 1, we spectroscopically assessed the complete cycle of CDN synthesis and hydrolysis:

The fluorescent NTPs were thus incubated with DncV and quenched with CIAP at designated time points (under the same conditions as DncV-mediated synthesis above). The samples were then digested with S1 nuclease to yield the free nucleosides. [32] This hydrolysis process was monitored by fluorescence spectroscopy. Similar to the results described above, the fluorescence intensity decreased upon incubation with DncV for both tzGTP (dashed or solid black lines in FIGS. 12A-12C) and $^{th}$GTP (dashed or solid blank lines FIGS. 12D-12F). Increasing fluorescence intensity was then observed upon administration of S1 nuclease to the DncV-mediated reaction mixtures, and the emission intensity at S1 endpoint is comparable to that of DncV at time 0 (colored lines in FIG. 12), as one would predict based on the model presented in FIG. 1. The same trends were observed for samples incubated with DncV for different amount of time (FIGS. 12C, 12F).

The recovery of emission after S1 nuclease mediated hydrolysis reactions further supports our model, suggesting that the fluorescence quenching observed during DncV-mediated CDN syntheses is caused by the spatial proximity of chromophores. While unlikely under our reaction conditions, intermolecular aromatic interactions could also contribute under certain circumstances, as CDNs have been reported to equilibrate between monomeric and intercalated dimeric structures. [27a]

CONCLUSIONS

Since the discovery of c-di-GMP in 1987, the landscape representing the signaling mechanisms and biological significance of CDNs has continued to expand. [1a,5b,27a,33] As second messengers, the intracellular concentration of CDNs is tightly modulated by multiple dinucleotide cyclases and phosphodiesterases (PDEs), which further impact bacterial homeostasis and virulence through CDN-regulated signaling machineries, including riboswitches and protein receptors. [5b,27a] In this study we have demonstrated the utility of novel isomorphic fluorescent analogues of this key bacterial messenger for monitoring the activity of a cyclase and both specific and non-specific phosphodiesterases in real-time. A comparison to traditional methods (e.g., HPLC) shows the fluorescence-based approach is reliable and much faster, making it amenable to further optimization and potential applications requiring higher throughput. The subtle structural differences between G and its emissive surrogates $^{th}$G and $^{tz}$G, provided insight into the molecular signatures governing the enzyme-substrate recognition.

Previous structural studies have illustrated that DncV belongs to a large family of nucleotidyltransferases (CD-NTases) that is responsible of synthesizing various types of CDNs as well as cyclic trinucleotides. [6] Recent reports have indicated that theses CD-NTases and their products might play distinctive roles in host-pathogen interactions, though detailed analyses are needed to further illustrate their function and signaling mechanism. [6] The isomorphic fluorescent NTPs and their CDNs described in this contribution could serve as powerful tools for the study of such processes in vitro, shed light on their recognition features and accelerate the fabrication of high throughput discovery assays for agonists and antagonists.

Methods and Materials

Preparation of fluorescent nucleosides and NTPs. Fluorescent nucleosides and NTPs were prepared according to previous publications. See Shin et al, *J. Am. Chem. Soc.* 2015, 137, 14602-14605; McCoy et al, *J. Am. Chem. Soc.* 2014, 36,15176-15184.

Cloning and protein expression. Plasmid with VC0179 (DncV) cloned in pDONR221 vector was purchase from DNASU Plasmid Repository. The gene of interest (GOI) was amplified and inserted into XhoI and NdeI digested pet28b vector by Gibson Assembly (New England Biolabs) following the manufacture's instruction. NEBuilder was used to design the GOI-vector overlapping PCR primers. The gene of interest was amplified by PCR with Q5 High-Fidelity DNA Polymerase (New England Biolabs) with forward primer and reverse primer shown in Supporting Information for Li et al, "Enzymatic Syntheses and Applicatins of Fluorescent Cyclic Dinucleotides," Chem Eur. J. 26:6076-6084 (Apr. 28, 2020). The insertion was confirmed by Sanger sequencing (GenScript).

PA3977 (rocR) gene fragment with 5'-NdeI and 3'-HindIII cleavage sites was purchase from Integreated DNA Technologies (gBlock® Gene Fragments). The GOI and pet28b vector were digested with NdeI and HindII to create matching sticky ends. The digested vector was also treated with CIAP (Promega) to avoid self-ligation. The digested GOI and vector were then ligated with T4 DNA ligase (New England Biolabs) following standard protocols. The insertion was confirmed by Sanger sequencing (GenScript)

Plasmids containing the gene of interest were transformed into Escherichia coli BL21(DE3) competent cells respectively for protein expression according to previous publications. See Barajas et al, Angew. Chem. Int. Ed. Engl. 2016, 55, 13005-13009; Barajas et al, Proc. Natl. Acad. Sci. U.S.A. 2017, 114, 4142-4148.

Enzymatic synthesis of c-di-GMP analogues. For large scale synthesis, 500 pM of guanosine 5'-triphosphates analogs were incubated with at 37° C. 2.3 pM of DncV in a buffer containing 0.1 M NaCI, 40 mM Tris pH 7.5 and 10 mM MgCl2 for 2-5 hours. The reaction mixture was then heated at 90° C. for 5 minutes and chilled on ice for 15 minutes and filtered through a 0.22 pm filter. The supernatant was separated by Synergi 4p Fusion-RP 80A column (250×10 mm, 4 pm particle size) or Sepax Bio C-18 column (250×10 mm, 5 pm particle size) with a gradient of 0.5-20% of 10 mM NH4OAc, pH 7 in MeOH in 20 minutes on an Agilent 1200 series HPLC system (Agilent Technologies). Collected HPLC fractions were lyophilized with Labconco FreeZone 2.5 lyophilizer and re-dissolved in autoclaved water. UV spectroscopy was used to determine the concentration of each solution with the following extinction coefficients: 26000 L mol$^{-1}$ cm$^{-1}$ for c-di-GMP (260 nm), 8370 L mol$^{-1}$ cm$^{-1}$ for c-di-IzGMP (333 nm), 7470 L mol$^{-1}$ cm$^{-1}$ for c-di-IhGMP (321 nm), 3735 L mol$^{-1}$ cm$^{-1}$ for c-Gth-GMP (321 nm), and 4185 L mol$^{-1}$ cm$^{-1}$ for c-GIzGMP (333 nm) (Supporting Experiments; Section 4 below).

For kinetics studies of c-di-GMP analogue synthesis, 500 pM of guanosine 5'-triphosphates analogs were incubated at 37° C. with 2.3 pM of DncV in a buffer containing 0.1 M NaCI, 40 mM Tris pH 7.5 and 10 mM MgCl2. 8 pL aliquots of reaction were taken out at designated time points, and added to quenching solution containing 30 pL of water and 1 pL of alkaline phosphatase CIAP (1 U/pL, Promega) and incubated at 37° C. for another 5 minutes. 30 pL of the mixture was subjected to HPLC analysis after filtration. The reaction mixture was separated by Sepax Bio C-18 column (250×10 mm, 5 pmparticle size) with a gradient of 0.5%-25% of 10 mM TEAA, pH7 in MeOH in 20 min at 25° C. on an Agilent 1200 series HPLC system (Agilent Technologies).

CDN hydrolysis with rocR. 10 pM of CDN was incubated with 100 nM of rocR in a buffer containing 100 mM Tris-HCI, pH 8, 20 mM KCI, 25 mM MgCl$_2$ at 37° C. Aliquots of the reaction mixture were taken out at designated time points and quenched with 100 mM CaCl2. All aliquots were filtered before subjected to reverse-phase HPLC analysis. The reaction mixture was separated by Sepax Bio C-18 column (250×10 mm, 5 pm particle size) with a gradient of 0.1-15% of 10 mM NH4OAc, pH7 in MeOH in 12 minutes at 25° C. or 50° C. (only for reactions of c-GtzGMP and c-di-tzGMP) on an Agilent 1200 series HPLC system (Agilent Technologies).

CDN synthesis and hydrolysis monitored with steady-state fluorescence spectroscopy. For CDN synthesis, 500 pM of guanosine 5'-triphosphates analogs were incubated at 37° C. with 2.3 pM of DncV in a buffer containing 0.1 M NaCI, 40 mM Tris pH 7.5 and 10 mM MgCl$_2$. The reactions were sampled at designated time points. Aliquots (7 pL) were taken out and added to quenching solution [120 pL of water and 1 pL of calf intestine alkaline phosphatase (CIAP, 1 U/pL, Promega)] and incubated at 37° C. for another 5 minutes. The solution was then transferred to a cuvette and emission spectra were taken (excitation at 380 nm, emission spectra were collected from 390 to 650 nm at 37° C.). The concentration of the starting material in the cuvette was 27.4 pM.

For CDN synthesis followed by S1 hydrolysis, DncV mediated synthesis was conducted and quenched in the same way as mentioned above. 50 U of S1 nuclease (Promega, 1 U/pL) was added to the reaction mixture after transferring to cuvette for spectroscopic analysis. Excitation wavelength=380 nm, emission spectra were collected from 390 nm to 650 nm at 37° C.

For rocR hydrolysis, 10 pM of CDN was incubated in cuvette with 100 nM of rocR in a buffer containing 100 mM Tris-HCI, pH 8, 20 mM KCI, 25 mM MgCl2 at 37° C.

Emission spectra were taken at each designated time points. Excitation wavelength=380 nm, emission spectra were collected from 390 to 650 nm.

Data Analysis and curve fitting. The corresponding emission spectrum or HPLC trace for each reaction time point was integrated using a trapezoidal Riemann sum. Specifically, for the HPLC monitored reactions, the integrated area under the peak for each species was corrected using an extinction coefficient and normalized to its relative concentration. The relative concentrations were plotted against time. A set of ordinary differential equations (ODEs) (Eqs. 1-4, 7-8, 10-13, 14-19) consistent with the mechanism shown in Scheme 1 or 2 was solved using the Runge-Kutta method with a variable time step in MatLab (function ode45). Initial concentrations of the substrate and enzyme used for each reaction were given above. The resulting fitted curves for each species were optimized by iteratively testing for k values (Tables 1, 3) that maximized $R^2$. For fluorescence-monitored reactions, the integrated emission intensity was plotted against time. The integrated emission intensity was converted to concentration using Eqs 5-6, 9, 20-21. The fitted curves were generated and optimized using the same ODEs and software settings mentioned above.

Absorption and Emission Spectra of CDNs and nucleosides. Absorption spectra were measured on a Shimadzu UV-2450 spectrophotometer setting the slit 1 nm and using a resolution of 0.5 nm. Steady state emission and excitation spectra were measured on a Horiba-Fluoromax-4 equipped with a cuvette holder with a stirring system setting both the excitation and emission slits at 3 nm, the resolution at 1 nm and the integration time at 0.1 s. The steady state emission spectra were recorded upon excitation at 380, 370, 360, 350, 340, 330, 320, 310, and 300 nm in that order respectively. All the emission spectra were corrected for the instrumental response.

All the spectra were blanked against MilliQ water. Both instruments were equipped with a thermostat-controlled ethylene glycol-water bath fitted to specially designed cuvette holder and the temperature was kept at 25.0±0.1° C.

In a typical experiment, aliquots of the concentrated stock solutions (aqueous solutions for all CDNs, and DMSO solutions for nucleosides) were diluted with Milli Q water to arrive at an optical density of −0.05 with a final volume of 125 pL (DMSO<0.5%). The solutions were mixed with a pipette for 10 seconds and placed in the cuvette holder and incubated at 25° C. for 3 minutes before spectra were recorded.

Fluorescence quantum yield determination. The samples concentrations were adjusted to have an optical density lower than 0.07 at the excitation wavelength ($A_e$x). The fluorescence quantum yield (0) were evaluated based on an external standard, 2-aminopurine (0.68 in water, Aex 320 nm) by using equation 22:

$$\Phi = \Phi_{STD} \frac{I}{I_{STD}} \frac{OD_{STD}}{OD} \frac{n^2}{n^2_{STD}} \quad (22)$$

Where cSTD is the fluorescence quantum yield of the standard, I and Ism are the integrated area of the emission band of the sample and the standard respectively, OD and ODsm are the optical density at the excitation wavelength for the sample and the standard respectively and n and nsTD are the solvent refractive index of the sample and the standard solutions respectively.

The extinction coefficient (E) of c-di-GMP (26000 L $mol^{-1}$ $cm^{-1}$ at 260 nm) was obtained from Whitney etl al, J. Biol. Chem., 2012, 287, 23582-23593. Assuming an additive effect of the two nucleosides at a defined wavelength and considering a hypochromic effect (10%) due to the stacked conformation, the theoretical extinction coefficients of the fluorescent CDNs were calculated from the extinction coefficients of the nucleosides at Aabs$^{max}$x using the following equation:

$$\varepsilon_{CDN} = (\varepsilon_1 + \varepsilon_2) \times 0.9 \quad (Eq\ S1)$$

where ε1 ε2 represent the extinction coefficients of the two nucleosides incorporated in the CDN. The extinction coefficients of thG (321 nm) and $^{12}$G (333 nm) were reported in previous publications. We assumed guanosine does not absorb at 321 nm or 333 nm.

The theoretical extinction coefficients for fluorescent CDNs are: 8370 L $mol^{-1}$ $cm^{-1}$ for c-di-$^1$zGMP (333 nm), 7470 L $mol^{-1}$ $cm^{-1}$ for c-di-$^{thGmp}$ (321 nm), 3735 L $mol^{-1}$ $cm^{-1}$ for c-G$^{1n}$GMP (321 nm), and 4185 L $mol^{-1}$ $cm^{-1}$ for c-GtzGMP (333 nm).

Figure 14:
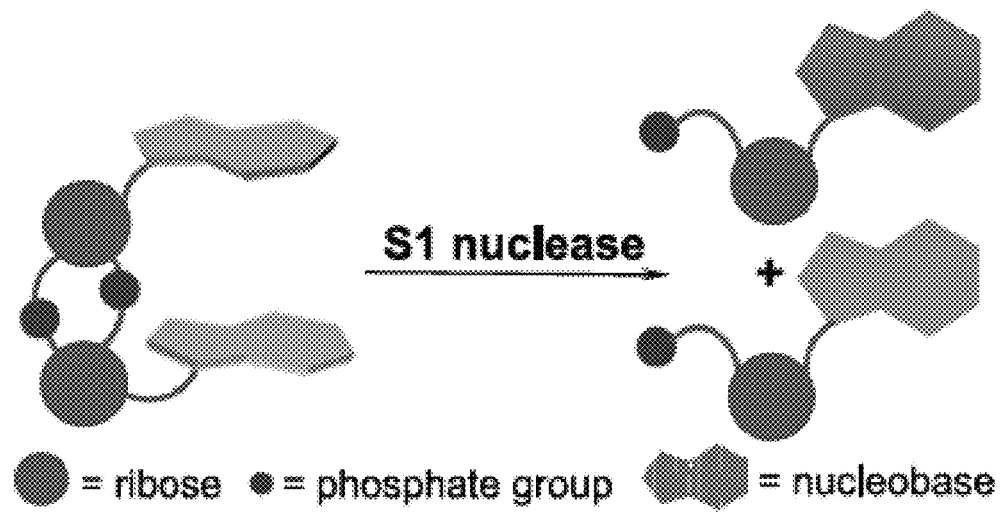
FIG. 14 shows the scheme of S1 nuclease-mediated hydrolysis of CDNs.

To validate the estimated extinction coefficients, we also hydrolyzed some of the CDNs into nucleoside monophosphates (NMPs) using S1 nuclease (FIG. 14), and calculated the extinction coefficients of CDNs by comparing the UV absorption of the samples before and after the hydrolysis.

CDN (7.4 NM) was incubated with S1 nuclease (50 U, purchased from Promega) in an acetate buffer (125 μL, 0.05 M sodium acetate, pH 4.5, 0.28 M NaCI, 0.45 mM ZnSO4) at 37° C. Absorption spectra were taken at each designated time points. All measurements were carried out in a 1 cm four-sided quartz cuvette from Helma. Absorption spectra were measured on a Shimadzu UV-2450 spectrophotometer equipped with a thermostat-controlled ethylene glycol-water bath fitted to specially designed cuvette holder and the temperature was kept at 37.0±0.1° C. The slit of the spectrophotometer was set at 1 nm and using a resolution of 0.5 nm.

The S1-mediated cleavage of the c-di-$^1$hGMP was depicted, over time, by a hyperchromic effect with no significant bathochromic shift on the absorption spectra (Figure S15$a$). The hyperchromicity at the reference wavelength for the concentration evaluation (321 nm) and at the absorption maxima (312 nm) was of 14% and 18%, respectively (calculated using Eq S2). The calculation based on the experimental assay provided a molar extinction coefficient at 321 nm equal to 7300 L marl $cm^{-1}$, which is in good agreement with the theoretically estimated value (7470 L $mol^{-1}$ $cm^{-1}$).

Relative Absorbance Intensity %=((Abs−Abs$_0$)/Abs$_0$)×100 (Eq S2)

The S1-mediated cleavage of the c-G$^1$hGMP was depicted, over time, by a hyperchromic effect along with mild bathochromic shift from 318 to 314 nm on the absorption spectra. The hyperchromicity at the reference wavelength for the concentration evaluation (321 nm) and at the absorption maxima (312 nm) was of 9% and 15% respectively (calculated using Eq S2). The calculation based on the experimental assay provided a molar extinction coefficient at 321 nm equal to 3690 L mol−1 $cm^{-1}$, which is in good agreement with the theoretical value (3735 L $mol^{-1}$ $cm^{-1}$). Since the experimentally calculated extinction coefficients were in good agreements with the theoretical values, we thus used theoretically calculated extinction coefficients for the determination of fluorescent CDNs.

Example 4

Figure 15:
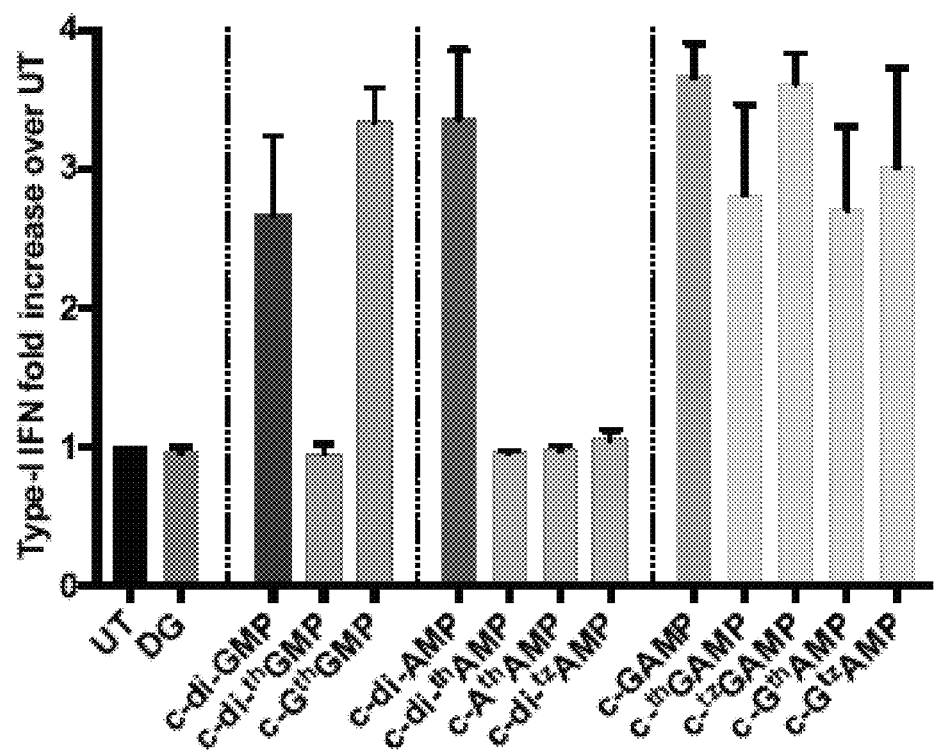
FIG. 15 shows the Type-1 IFN induction in THP-1 cells by the STING agonists described herein. Error bars indicate SD.

THP-1 cells were seeded at a density of 100,000 cells/well in a 96-well cell culture plate and differentiated with 25 nM of PMA for approximately 20 h prior to treatment with the CDNs (i.e., c-di-$^{tz}$GMP, c-di-$^{th}$GMP, c-G$^{th}$GMP, c-G$^{tz}$GMP, c-GAMP, c-$^{th}$GMP, c-$^{tz}$GAMP, c-G$^{th}$AMP, c-G$^{tz}$AMP, c-di-$^{th}$AMP, c-di-$^{tz}$AMP, c-di-AMP, and c-di-GMP). Cells were transfected with 5 μM of the CDNs in a permeabilization buffer containing 5 μg/mL of digitonin, then washed and incubated in RPMI medium with 2% FBS at 37° C. for 4 h. 50 μL of cell culture supernatant per well was transferred to 150 μL of HEK-Blue IFN α/β reporter cells seeded at 50,000 cells/well in a 96-well cell culture plate and incubated at 37° C. overnight. The reporter cells were spin down the next day, and 50 μL of cell culture supernatant per well was transferred to a 96-well plate and added with 150 μL of QUANTI-Blue™ SEAP detection medium ((InvivoGen). The samples were then incubated at 37° C. for 1 h 20 min before absorption was measured at 640 nm. The absorption signal of each sample was normalized to untreated samples. One or two independent assays were done in duplicates or triplicates. The results are shown in FIG. 15.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

REFERENCES FOR EXAMPLE 2

[1] R. Medzhitov, C. A. Janeway Jr, Cell 1997, 91, 295-298. [2] S. Akira, Immunol. Rev. 2009, 227, 5-8. [3] a) S. Gordon, Cell 2002, 111, 927-930; b) O. Takeuchi, S. Akira, Cell 2010, 140, 805-820. [4] A. Iwasaki, R. Medzhitov, Science 2010, 327, 291-295. [5] a) M. Motwani, S. Pesiridis, K. A. Fitzgerald, Nat. Rev. Genet. 2019, 20, 657-674; b) A. P. McFarland, S. Luo, F. Ahmed-Qadri, M. Zuck, E. F. Thayer, Y. A. Goo, K. Hybiske, L. Tong, J. J. Woodward, Immunity 2017, 46, 433-445; c) A. Ablasser, Z. J. Chen, Science 2019, 363, eaat8657. [6] D. L. Burdette, K. M. Monroe, K. Sotelo-Troha, J. S. Twig, B. Eckert, M. Hyodo, Y. Hayakawa, R. E. Vance, Nature 2011, 478, 515-518. [7] a) L. Sun, J. Wu, F. Du, X. Chen, Z. J. Chen, Science 2013, 339, 786-791; b) J. Wu, L. Sun, X. Chen, F. Du, H. Shi, C. Chen, Z. J. Chen, Science 2013, 339, 826-830; c) E. J. Diner, D. L. Burdette, S. C. Wilson, K. M. Monroe, C. A. Kellenberger, M. Hyodo, Y. Hayakawa, M. C. Hammond, R. E. Vance, Cell Rep. 2013, 3, 1355-1361. [8] a) P. Gao, M. Ascano, T. Zillinger, W. Wang, P. Dai, A. A. Serganov, B. L. Gaffney, S. Shuman, R. A. Jones, L. Deng, G. Hartmann, W. Barchet, T. Tuschl, D. J. Patel, Cell 2013, 154, 748-762; b) Q. Chen, L. Sun, Z. J. Chen, Nat. Immunol. 2016, 17, 1142-1149; c) S. Liu, X. Cai, J. Wu, Q. Cong, X. Chen, T. Li, F. Du, J. Ren, Y.-T. Wu, N. V. Grishin, Z. J. Chen, Science 2015, 347, aaa2630. [9] S. R. Margolis, S. C. Wilson, R. E. Vance, Trends Immunol. 2017, 38, 733-743. [10] a) H. Chen, H. Sun, F. You, W. Sun, X. Zhou, L. Chen, J. Yang, Y. Wang, H. Tang, Y. Guan, W. Xia, J. Gu, H. Ishikawa, D. Gutman, G. Barber, Z. Qin, Z. Jiang, Cell 2011, 147, 436-446; b) T. Abe, G. N. Barber, J. Virol. 2014, 88, 5328-5341. [11] a) J. Fu, D. B. Kanne, M. Leong, L. H. Glickman, S. M. McWhirter, E. Lemmens, K. Mechette, J. J. Leong, P. Lauer, W. Liu, K. E. Sivick, Q. Zeng, K. C. Soares, L. Zheng, D. A. Portnoy, J. J. Woodward, D. M. Pardoll, T. W. Dubensky Jr, Y. Kim, Sci. Transl. Med. 2015, 7, 283ra252; b) A. Li, M. Yi, S. Qin, Y. Song, Q. Chu, K. Wu, J. Hematol. Oncol. 2019, 12, 35. [12] a) L. Corrales, L. H. Glickman, S. M. McWhirter, D. B. Kanne, K. E. Sivick, G. E. Katibah, S. R. Woo, E. Lemmens, T. Banda, J. J. Leong, K. Metchette, T. W. Dubensky Jr., T. F. Gajewski, Cell Rep. 2015, 11, 1018-1030; b) L. Li, Q. Yin, P. Kuss, Z. Maliga, J. L. Millan, H. Wu, T. J. Mitchison, Nat. Chem. Biol. 2014, 10, 1043-1048. [13] a) B. Novotná, L. Vaneková, M. Zavřel, M. Buděšínský, M. Dejmek, M. Smola, O. Gutten, Z. A. Tehrani, M. Pimková Polidarová, A. Brázdová, R. Liboska, I. Štěpánek, Z. Vavřina, T. Jandušík, R. Nencka, L. Rulíšek, E. Boura, J. Brynda, O. Páv, G. Birkuš, J. Med. Chem. 2019, 62, 10676-10690; b) K. D. Launer-Felty, S. A. Strobel, Nucleic Acids Res. 2018, 46, 2765-2776. [14] a) C. Wang, M. Sinn, J. Stifel, A. C. Heiler, A. Sommershof, J. S. Hartig, J. Am. Chem. Soc. 2017, 139, 16154-16160; b) C. A. Shanahan, S. A. Strobel, Org. Biomol. Chem. 2012, 10, 9113-9129; c) Y. Luo, J. Zhou, S. K. Watt, V. T. Lee, T. K. Dayie, H. O. Sintim, Mol. BioSyst. 2012, 8, 772-728; d) J. Zhou, Y. Zheng, B. T. Roembke, S. M. Robinson, C. Opoku-Temeng, D. A. Sayre, H. O. Sintim, RSC Adv. 2017, 7, 5421-5426; e) B. T. Roembke, J. Zhou, Y. Zheng, D. Sayre, A. Lizardo, L. Bernard, H. O. Sintim, Mol. BioSyst. 2014, 10, 1568-1575; f) P. Clivio, S. Coantic-Castex, D. Guillaume, Chem. Rev. 2013, 113, 7354-7401. [15] a) D. Shin, R. W. Sinkeldam, Y. Tor, J. Am. Chem. Soc. 2011, 133, 14912-14915; b) A. R. Rovira, A. Fin, Y. Tor, J. Am. Chem. Soc. 2015, 137, 14602-14605; c) Y. Li, P. T. Ludford III, A. Fin, A. R. Rovira, Y. Tor, Chem. Eur. J. 2020, 27, 6076-6084. [16] S. E. Girardin, I. G. Boneca, L. A. M. Carneiro, A. Antignac, M. Jéhanno, J. Viala, K. Tedin, M. Taha, A. Labigne, U. Zäthringer, A. J. Coyle, P. S. DiStefano, J. Bertin, P. J. Sansonetti, D. J. Philpott, Science 2003, 300, 1584-1587. [17] a) H. Konno, K. Konno, G. N. Barber, Cell 2013, 155, 688-698; b) R. A. Porritt, P. J. Hertzog, Trends Immunol. 2015, 36, 150-160. [18] a) P. Gao, T. Zillinger, W. Wang, M. Ascano, P. Dai, G. Hartmann, T. Tuschl, L. Deng, W. Barchet, D. J. Patel, Cell Rep. 2014, 8, 1668-1676; b) G. Yi, V. P. Brendel, C. Shu, P. Li, S. Palanathan, C. Cheng Kao, PLoS One 2013, 8, e77846. [19] X. Zhang, H. Shi, J. Wu, X. Zhang, L. Sun, C. Chen, Z. J. Chen, Mol. Cell 2013, 51, 226-235.

REFERENCES FOR EXAMPLE 3

[1] a) U. Jenal, A. Reinders, C. Lori, Nat. Rev. Microbiol. 2017, 15, 271-284; b) R. M. Corrigan, A. Grundling, Nat. Rev. Microbiol. 2013, 11, 513-524. [2] O. Danilchanka, J. J. Mekalanos, Cell 2013, 154, 962-970. [3] a) X. Zhang, H. Shi, J. Wu, X. Zhang, L. Sun, C. Chen, Z. J. Chen, Mol. Cell 2013, 51, 226-235; b) P. Gao, M. Ascano, Y. Wu, W. Barchet, B. L. Gaffney, T. Zillinger, A. A. Serganov, Y.

Liu, R. A. Jones, G. Hartmann, T. Tuschl, D. J. Patel, *Cell* 2013, 153, 1094-1107; c) Q. Chen, L. Sun, Z. J. Chen, *Nat. Immunol.* 2016, 17, 1142-1149. [4] A. P. McFarland, S. Luo, F. Ahmed-Qadri, M. Zuck, E. F. Thayer, Y. A. Goo, K. Hybiske, L. Tong, J. J. Woodward, *Immunity* 2017, 46, 433-445. [5] a) P. V. Krasteva, H. Sondermann, *Nat. Chem. Biol.* 2017, 13, 350-359; b) D. Kalia, G. Merey, S. Nakayama, Y. Zheng, J. Zhou, Y. Luo, M. Guo, B. T. Roembke, H. O. Sintim, *Chem. Soc. Rev.* 2013, 42, 305-341. [6] A. T. Whiteley, J. B. Eaglesham, C. C. de Oliveira Mann, B. R. Morehouse, B. Lowey, E. A. Nieminen, O. Danilchanka, D. S. King, A. S. Y. Lee, J. J. Me-kalanos, P. J. Kranzusch, *Nature* 2019, 567, 194-199. [7] a) E. J. Diner, D. L. Burdette, S. C. Wilson, K. M. Monroe, C. A. Kellenberg-er, M. Hyodo, Y. Hayakawa, M. C. Hammond, R. E. Vance, *Cell Rep.* 2013, 3, 1355-1361; b) K. D. Launer-Felty, S. A. Strobel, *Nucleic Acids Res.* 2018, 46, 2765-2776. [8] T. Fahmi, G. C. Port, K. H. Cho, *Genes* (Basel) 2017, 8, 197. [9] J. Zhou, Y. Zheng, B. T. Roembke, S. M. Robinson, C. Opoku-Temeng, D. A. Sayre, H. O. Sintim, *RSC Adv.* 2017, 7, 5421-5426. [10] R. W. Sinkeldam, N. J. Greco, Y. Tor, *Chem. Rev.* 2010, 110, 2579-2619. [11] a) D. Shin, R. W. Sinkeldam, Y. Tor, *J. Am. Chem. Soc.* 2011, 133, 14912-14915; b) A. R. Rovira, A. Fin, Y. Tor, *J. Am. Chem. Soc.* 2015, 137, 14602-14605. [12] a) Y. Li, A. Fin, L. McCoy, Y. Tor, *Angew. Chem. Int. Ed.* 2017, 56, 1303-1307; *Angew. Chem.* 2017, 129, 1323-1327; b) L. S. McCoy, D. Shin, Y. Tor, *J. Am. Chem. Soc.* 2014, 136, 15176-15184; c) F. Hallé, A. Fin, A. R. Rovira, Y. Tor, *Angew. Chem. Int. Ed.* 2018, 57, 1087-1090; *Angew. Chem.* 2018, 130, 1099-1102; d) J. Feldmann, Y. Li, Y. Tor, *Chem. Eur. J.* 2019, 25, 4379-4389. [13] M. Gentner, M. G. Allan, F. Zaehringer, T. Schirmer, S. Grzesiek, *J. Am. Chem. Soc.* 2012, 134, 1019-1029. [14] a) Y. Luo, J. Zhou, S. K. Watt, V. T. Lee, T. K. Dayie, H. O. Sintim, *Mol. Bio-syst.* 2012, 8, 772-728; b) C. A. Shanahan, B. L. Gaffney, R. A. Jones, S. A. Strobel, *J. Am. Chem. Soc.* 2011, 133, 15578-15592; c) C. A. Shanahan, S. A. Strobel, *Org. Biomol. Chem.* 2012, 10, 9113-9129. [15] a) P. Clivio, S. Coantic-Castex, D. Guillaume, *Chem. Rev.* 2013, 113, 7354-7401; b) C. Wang, M. Sinn, J. Stifel, A. C. Heiler, A. Sommershof, J. S. Hartig, *J. Am. Chem. Soc.* 2017, 139, 16154-16160. [16] a) B. W. Davies, R. W. Bogard, T. S. Young, J. J. Mekalanos, *Cell* 2012, 149, 358-370; b) K. Kato, R. Ishii, S. Hirano, R. Ishitani, O. Nureki, *Structure* 2015, 23, 843-850; c) Y. Lv, Q. Sun, X. Wang, Y. Lu, Y. Li, H. Yuan, J. Zhu, D. Zhu, *Front. Microbiol.* 2019, 10, https://doi.org/10.3389/fmicb.2019.02111. [17] P. J. Kranzusch, A. S. Y. Lee, S. C. Wilson, M. S. Solovykh, R. E. Vance, J. M. Berger, J. A. Doudna, *Cell* 2014, 158, 1011-1021. [18] Z. Ming, W. Wang, Y. Xie, P. Ding, Y. Chen, D. Jin, Y. Sun, B. Xia, L. Yan, Z. Lou, *Cell Res.* 2014, 24, 1270-1273. [19] This dephosphorylation step simplifies the HPLC analyses. [20] D. Zhu, L. Wang, G. Shang, X. Liu, J. Zhu, D. Lu, L. Wang, B. Kan, J. R. Zhang, Y. Xiang, Mol. Cell 2014, 55, 931-937. [21] Such behavior is commonly observed for consecutive reactions; See: J. E. Espenson, *Chemical Kinetics and Reaction Mechanisms*, 2nd ed., McGraw-Hill, New York, 1995. [22] In all cases $k_1$ is much smaller than $k_2$. [23] Note that $I_1$ and $I_2$ were not experimentally differentiated in the kinetic analysis and are shown as $I=I_1+I_2$ in FIGS. 6C, 6F, 6I. [24] N. J. Hestand, F. C. Spano, *Chem. Rev.* 2018, 118, 7069-7163. [25] M. Sholokh, R. Improta, M. Mori, R. Sharma, C. Kenfack, D. Shin, K. Voltz, R. H. Stote, O. A. Zaporozhets, M. Botta, Y. Tor, Y. Mely, *Angew. Chem. Int.*

*Ed.* 2016, 55, 7974-7978; *Angew. Chem.* 2016, 128, 8106-8110. [26] A. R. Rovira, A. Fin, Y. Tor, *J. Am. Chem. Soc.* 2017, 139, 15556-15559. [27] a) U. Romling, M. Y. Galperin, M. Gomelsky, *Microbiol. Mol. Biol. Rev.* 2013, 77, 1-52; b) J. Rossello, A. Lima, M. Gil, J. Rodriguez Duarte, A. Correa, P. C. Carvalho, A. Kierbel, R. Duran, *Sci. Rep.* 2017, 7, 10281; c) F. Rao, Y. Yang, Y. Qi, Z. X. Liang, *J. Bacteriol.* 2008, 190, 3622-3631. [28] a) Y. Zheng, G. Tsuji, C. Opoku-Temeng, H. O. Sintim, *Chem. Sci.* 2016, 7, 6238-6244; b) A. J. Schmidt, D. A. Ryjenkov, M. Gomelsky, *J. Bacteriol.* 2005, 187, 477-481. [29] M. W. Chen, M. Kotaka, C. Vonrhein, G. Bricogne, F. Rao, M. L. Chuah, D. Svergun, G. Schneider, Z. X. Liang, J. Lescar, *J. Bacteriol.* 2012, 194, 4837-4846. [30 G. Minasov, S. Padavattan, L. Shuvalova, J. S. Brunzelle, D. J. Miller, A. Basle, C. Massa, F. R. Collart, T. Schirmer, W. F. Anderson, *J. Biol. Chem.* 2009, 284, 13174-13184. [31] We assumed that $P_1$ and $P_2$ in Scheme 2b has similar a values. [32] CIAP was still in the reaction mixture, therefore all the terminal phosphate groups will be removed and leaves free nucleosides instead of nucleoside monophosphates. [33] a) R. Libanova, P. D. Becker, C. A. Guzman, *Microb. Biotechnol.* 2012, 5, 168-176; b) P. Ross, H. Weinhouse, Y. Aloni, D. Michaeli, P. Weinberger-Ohana, R. Mayer, S. Braun, E. de Vroom, G. A. van der Marel, J. H. van Boom, M. Benziman, *Nature* 1987, 325, 279-281.

What is claimed is:

1. A compound, wherein the compound is a compound of Formula (I), a compound of Formula (II), a compound of Formula (III), a stereoisomer of one of the foregoing, or a pharmaceutically acceptable salt of one of the foregoing:

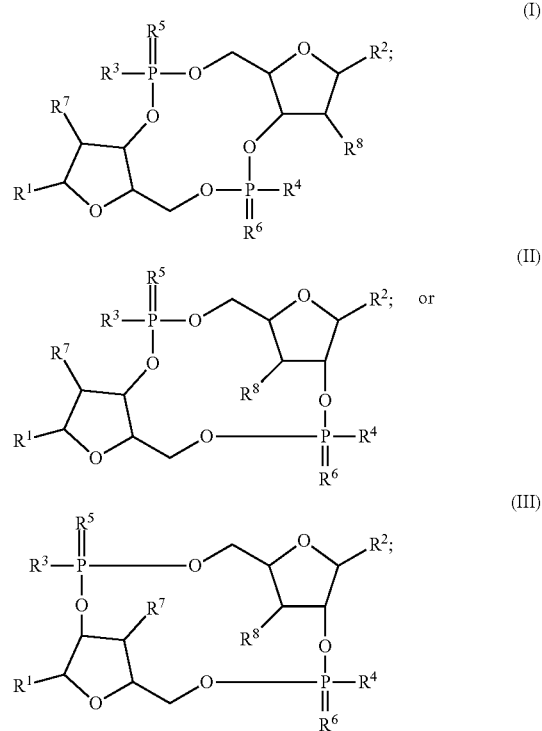

wherein:

R[1] and R[2] are each independently

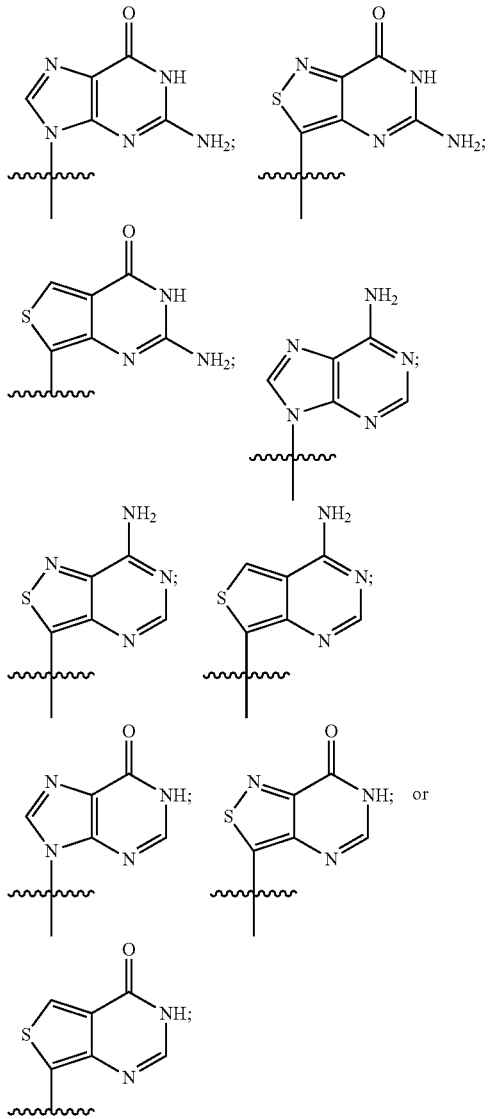

provided that at least one of R[1] and R[2] is:

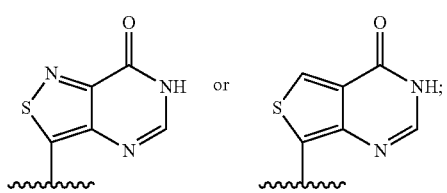 [SMILES: *c1snc2c(=O)[nH]cnc12 ; *c1scc2c(=O)[nH]cnc12]

R[3] and R[4] are each independently —SH or —OH;
R[5] and R[6] are each independently O or S; and
R[7] and R[8] are each independently halogen, H, —OH, or —OCH$_3$.

2. The compound of claim 1, wherein the compound is the stereoisomer of the compound of Formula (I), the stereoisomer of the compound of Formula (II), or the stereoisomer of the compound of Formula (III);

wherein the stereoisomer of the compound of Formula (I) is:

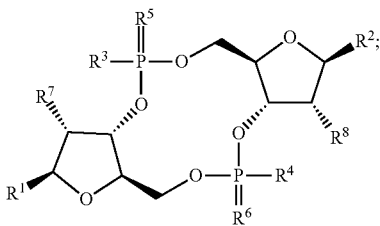

wherein the stereoisomer of the compound of Formula (II) is

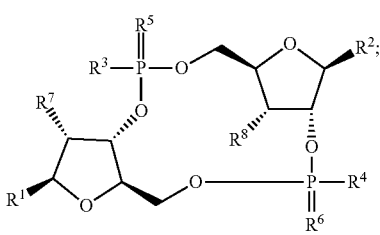

and wherein the stereoisomer of the compound of Formula (III) is

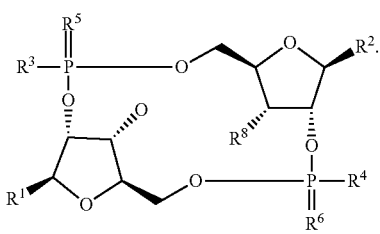

3. The compound of claim 1, wherein the compound is the stereoisomer of the compound of Formula (I) or the pharmaceutically acceptable salt of the compound of Formula (I);

wherein the stereoisomer of the compound of Formula (I) is

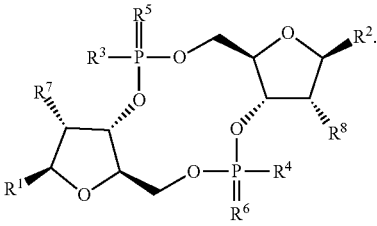

4. The compound of claim 1, wherein R[5] and R[6] are O.

5. The compound of claim 1, wherein R[7] and R[8] are —OH.

6. The compound of claim 1, wherein $R^1$ and $R^2$ are both

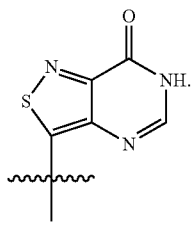 [SMILES: *c1snc2c(=O)[nH]cnc12]

7. A pharmaceutical composition comprising the compound of claim 1 and a pharmaceutically acceptable excipient.

8. A vaccine comprising the compound of claim 1 and an adjuvant.

9. A method for increasing an immune response in a patient in need thereof, the method comprising administering to the patient an effective amount of the compound of claim 1.

10. A method for treating cancer, an autoimmune disease, an inflammatory disease, an infectious disease, or a viral disease in a patient in need thereof, the method comprising administering to the patient an effective amount of the compound of claim 1.

11. A method for activating a STING protein, the method comprising contacting the STING protein with the compound of claim 1.

12. The compound of claim 1, wherein the compound is the stereoisomer of the compound of Formula (II) or the pharmaceutically acceptable salt thereof; wherein the stereoisomer of the compound of Formula (II) is

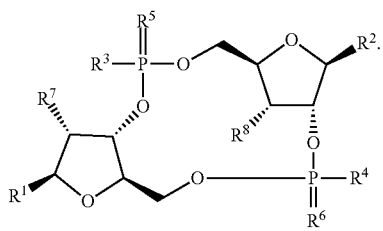

13. The compound of claim 1, wherein the compound is the stereoisomer of the compound of Formula (III) or the pharmaceutically acceptable salt thereof; wherein the stereoisomer of the compound of Formula (III) is

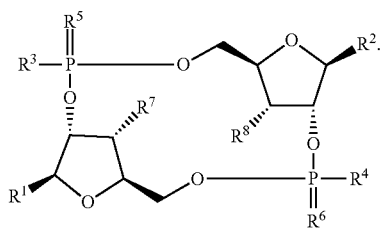

14. The compound of claim 1, wherein $R^1$ and $R^2$ are both

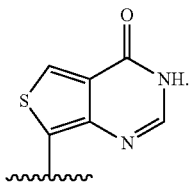 [SMILES: *c1scc2c(=O)[nH]cnc12]

15. The compound of claim 1, wherein $R^1$ is:

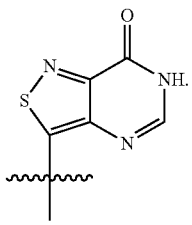 [SMILES: *c1snc2c(=O)[nH]cnc12]

16. The compound of claim 15, wherein $R^2$ is

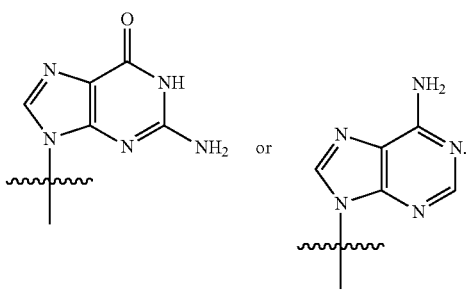 [SMILES: *n1cnc2c(=O)[nH]c(N)nc21 ; *n1cnc2c(N)ncnc21]

17. The compound of claim 1, wherein $R^1$ is:

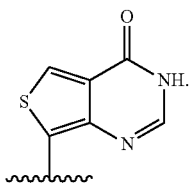

18. The compound of claim 17, wherein $R^2$ is

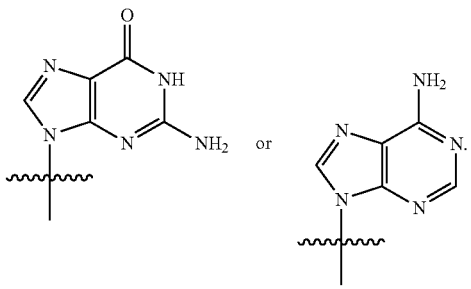 [SMILES: *n1cnc2c(=O)[nH]c(N)nc21 ; *n1cnc2c(N)ncnc21]

* * * * *